United States Patent
Schach Von Wittenau

(10) Patent No.: US 6,535,837 B1
(45) Date of Patent: Mar. 18, 2003

(54) CORRELATED HISTOGRAM REPRESENTATION OF MONTE CARLO DERIVED MEDICAL ACCELERATOR PHOTON-OUTPUT PHASE SPACE

(75) Inventor: Alexis E. Schach Von Wittenau, Livermore, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/520,287

(22) Filed: Mar. 7, 2000

Related U.S. Application Data

(60) Provisional application No. 60/123,242, filed on Mar. 8, 1999.

(51) Int. Cl.[7] ................................................. A61N 5/10
(52) U.S. Cl. ........................ 702/180; 702/72; 702/179; 378/64; 378/65; 600/407
(58) Field of Search ........................... 702/40, 49, 72, 702/94, 95, 106, 109, 110, 134, 141, 179, 180, 181, 189–199; 378/51, 64, 65; 514/323; 600/407

(56) References Cited

U.S. PATENT DOCUMENTS

| | | | | |
|---|---|---|---|---|
| 4,726,046 A | * | 2/1988 | Nunan | 378/65 |
| 5,418,715 A | * | 5/1995 | Deasy | 378/65 |
| 5,458,125 A | * | 10/1995 | Schweikard | 128/653.1 |
| 5,513,238 A | * | 4/1996 | Leber et al. | 378/65 |
| 5,740,225 A | * | 4/1998 | Nabatame | 378/65 |
| 5,802,136 A | * | 9/1998 | Carol | 378/65 |
| 5,859,891 A | * | 1/1999 | Hibbard | 378/62 |
| 5,870,697 A | * | 2/1999 | Chandler et al. | 702/179 |
| 6,029,079 A | * | 2/2000 | Cox et al. | 600/407 |
| 6,038,283 A | * | 3/2000 | Carol et al. | 378/65 |
| 6,134,296 A | * | 10/2000 | Siochi | 378/65 |
| 6,148,272 A | * | 11/2000 | Bergstrom et al. | 702/179 |
| 6,285,969 B1 | * | 11/2001 | Svatos | 703/2 |

* cited by examiner

*Primary Examiner*—Marc S. Hoff
*Assistant Examiner*—Jeffrey R West
(74) *Attorney, Agent, or Firm*—John P. Woolridge; Alan H. Thompson

(57) ABSTRACT

A method is provided to represent the calculated phase space of photons emanating from medical accelerators used in photon teletherapy. The method reproduces the energy distributions and trajectories of the photons originating in the bremsstrahlung target and of photons scattered by components within the accelerator head. The method reproduces the energy and directional information from sources up to several centimeters in radial extent, so it is expected to generalize well to accelerators made by different manufacturers. The method is computationally both fast and efficient overall sampling efficiency of 80% or higher for most field sizes. The computational cost is independent of the number of beams used in the treatment plan.

19 Claims, 17 Drawing Sheets

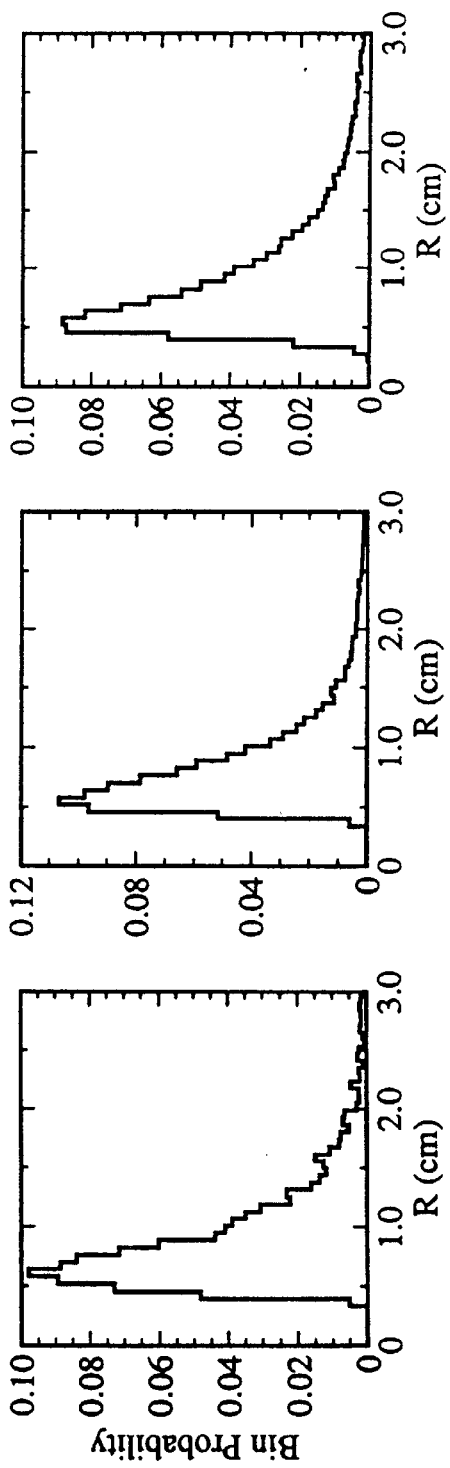
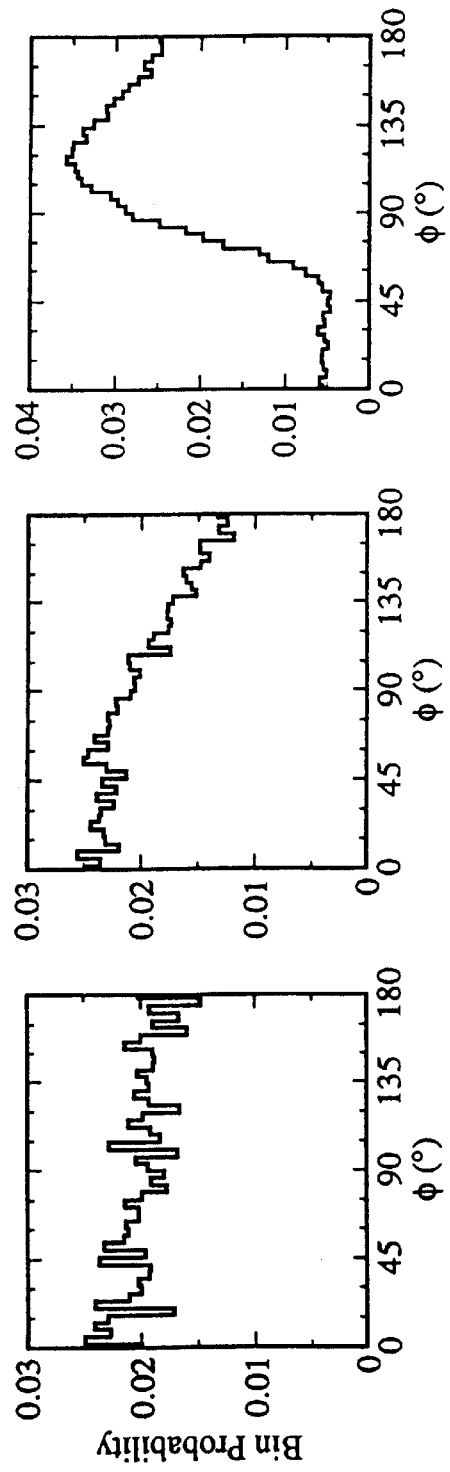
FIG. 9A FIG. 9C FIG. 9E
FIG. 9B FIG. 9D FIG. 9F

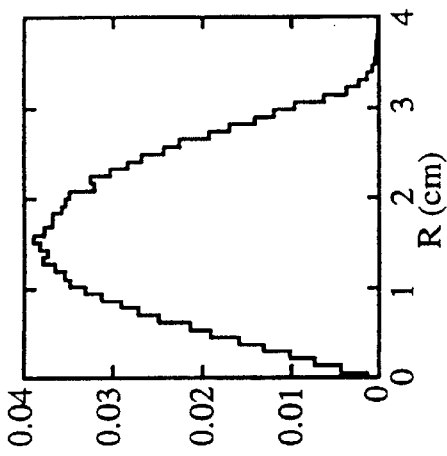
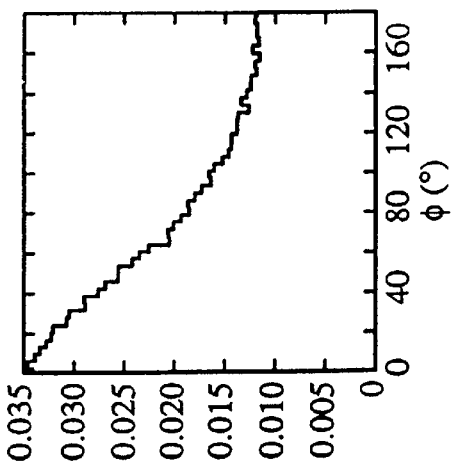
FIG. 10A  FIG. 10B
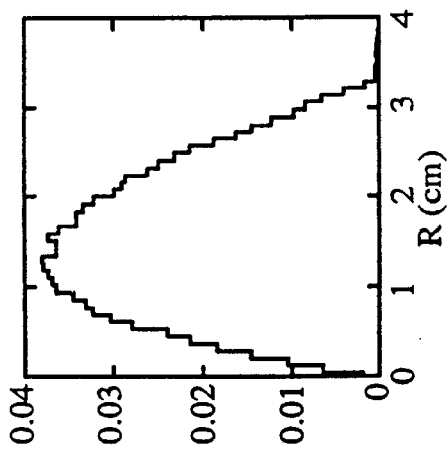
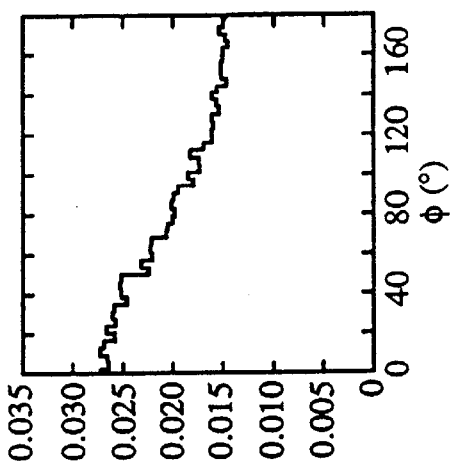
FIG. 10C  FIG. 10D
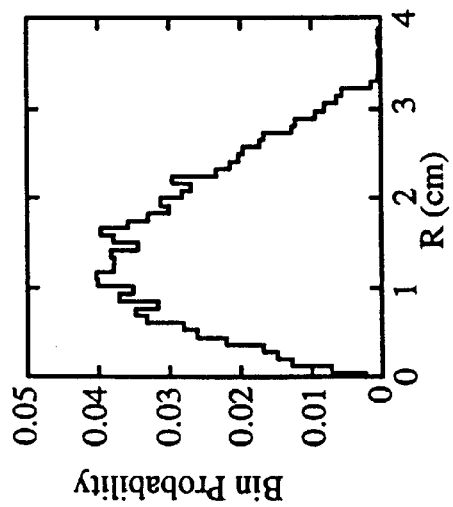
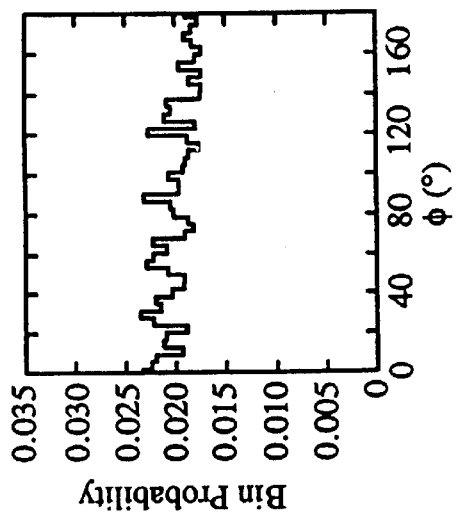
FIG. 10E  FIG. 10F

CORRELATED HISTOGRAM REPRESENTATION OF MONTE CARLO DERIVED MEDICAL ACCELERATOR PHOTON-OUTPUT PHASE SPACE

This patent application claims priority to U.S. Provisional Patent Application Serial No. 60/123,242 filed Mar. 8, 1999.

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates radiation therapy, and more specifically it relates to a method for condensing the photon energy and angular distributions obtained from Monte Carlo simulations of medical accelerators.

2. Description of Related Art

Monte Carlo methods are valuable for radiation dose calculations because of their ability to predict dose accurately for the entire range of conditions encountered in radiation treatment of cancer. They can correctly characterize beams of electrons and photons emerging from a linear accelerator, as well as photons, electrons and alpha particles emerging from brachytherapy sources. They can further accurately simulate the transport of particles through beam shaping devices or, for brachytherapy, source shielding devices. The transport of the resulting particles through the patient may then similarly be simulated, taking into account surface irregularities and the internal structure of the patient, including any metallic implants and prostheses, to determine the dose deposited in the patient. This disclosure provides photon treatments with linear accelerators.

While Monte Carlo methods are the most accurate means of predicting radiation dose, the use of generalized Monte Carlo software packages for routine clinical applications is presently impractical due partly to computer constraints, in particular, the running time needed to obtain a converged calculation. The lengthy running time of generalized Monte Carlo software packages warrants the development of algorithms optimized specifically for the problem at hand. The problem may be divided into three steps: (1) Determining the characteristics of the photon radiation emanating from the accelerator head; (2) propagating this radiation down to the patient, through beam modifiers (if any) and through the air above the patient; and (3), the actual transport within the patient of the original radiation, as well as of any radiation produced or scattered between the accelerator head and the patient.

SUMMARY OF THE INVENTION

It is an object of the present invention to provide, inter alia, a method for condensing the photon energy and angular distributions obtained from Monte Carlo simulations of medical accelerators. This method represents the output as a series of correlated histograms and as such is well-suited for inclusion as the photon-source package for Monte Carlo codes used to determine the dose distributions in photon teletherapy.

The method accounts for the isocenter-plane variations of the photon energy spectral distributions with increasing distance from the beam central axis for radiation produced in the bremsstrahlung target as well as for radiation scattered by the various treatment machine components within the accelerator head. Comparison of the isocenter energy fluence computed by this algorithm with that of the underlying full-physics Monte Carlo photon phase-space indicates that energy fluence errors are less than 1% of the maximum energy fluence for a range of open-field sizes. Comparison of jaw-edge penumbrae shows that the angular distributions of the photons are accurately reproduced. The Monte Carlo sampling efficiency (the fraction of generated photons which clear the collimator jaws) of the algorithm is approximately 83 % for an open 10×10 field, rising to approximately 96% for an open 40×40 field. Data file sizes for a typical medical accelerator, at a given energy, are approximately 150 kB, compared to the 1 GB size of the underlying full-physics phase-space file.

BRIEF DESCRIPTION OF THE DRAWINGS

FIGS. 9A–9E show closeup views of the radial and angular distributions used to generate the starting positions of the primary collimator photos.

FIGS. 10A–10F show closeup views of the radial and angular distributions used to generate the starting positions of the flattening filter photons.

DETAILED DESCRIPTION OF THE INVENTION

This disclosure focuses on Step 1, as described above in the Background section, determining the characteristics of the photon radiation emanating from the accelerator head. This step may be called the "patient-independent" part of the overall calculation, since the radiation output of the accelerator head is not affected by the presence of downstream beam modifiers. Steps 2 and 3 described in the Background section will necessarily vary from treatment plan to treatment plan, and may be called "patient-dependent" portions of the overall dose calculation. Step 1 merits a detailed treatment for two reasons. The first is that it is not purposeful to re-simulate the accelerator output during each new treatment plan; the time is better spent on the patient-specific part of the problem. The second reason is practical: Monte Carlo simulations of a medical accelerator head require a prohibitively long time to perform (many tens of hours on single-CPU machines), and it is impractical to store and manipulate (on a routine basis) the resulting gigabyte-size data files.

The problem, then, becomes one of developing a method to generate photons whose energies and trajectories represent those of the underlying Monte Carlo simulation of the accelerator head. Three issues arise in this context. First, the energy distributions and angular distributions of the photons generated by any such algorithm must accurately simulate those found in the underlying gigabyte-size data files. Second, the algorithm used to generate these photons must be computationally efficient, so that the running time of the overall dose calculation is not affected. Third, if the algorithm relies on condensing the gigabyte-size files into smaller data files for use during run-time, this process of condensation should be automated so that data files may be easily produced for a number of accelerators.

Several references suggest that dose delivered to the patient should be accurate to within 5% and that the computed dose should be accurate to within 2% of the maximum dose delivered to the patient. Therefore, the phase-space information must also be at least as accurate, and any algorithm used for sampling particles from the phase-space must produce data that is equally accurate. Furthermore, the sampling algorithm must be computationally efficient so as not to affect computational efficiency and the overall run-time.

Figure 1:
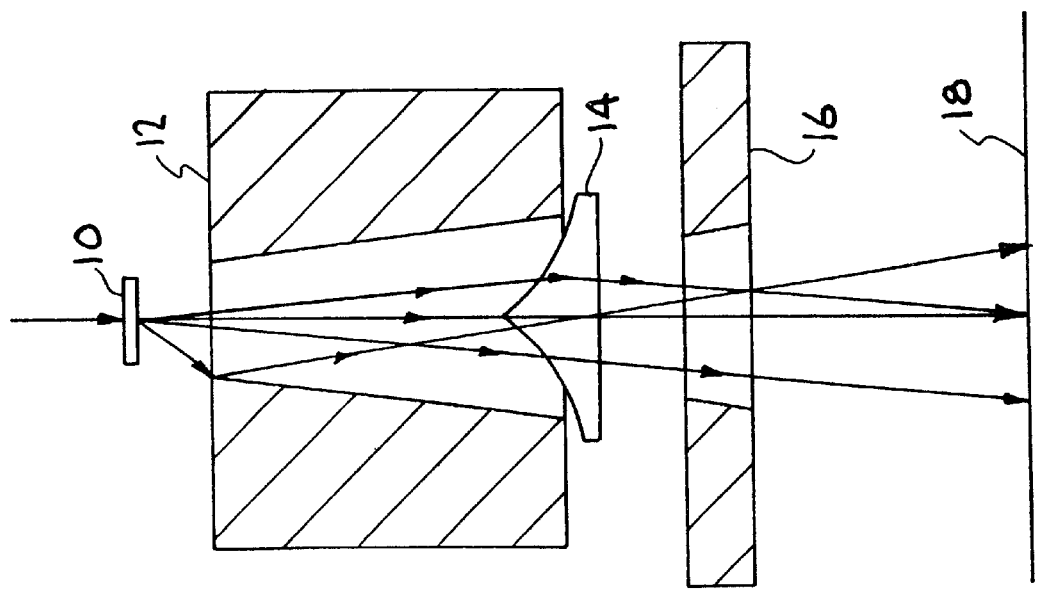
FIG. 1 shows a high-energy electron beam strikes a thin, high-Z target.

The nature of the source modeling problem is illustrated in FIG. 1. A beam of electrons strikes a thin target 10 made of a high-Z material. The resulting bremsstrahlung photons are collimated by a conical collimator 12. The photon beam passes through a flattening filter 14, which is thicker in the center and therefore attenuates the central portion of the bremsstrahlung photon distribution relative to the edges. The intended result is a flat dose distribution at a specified depth in a water phantom. Although the dose distribution is uniform, the photon energy fluence and energy spectrum vary as a function of distance from the central ray. There are two reasons for this. The first is that the energy of the bremsstrahlung photons decreases with increased scattering angle. The second is that the flattening filter removes more low-energy photons from the center of the beam than from the edge.

In addition, non-negligible amounts of radiation scatter from the collimator and the flattening filter and pass through the jaws 16 to arrive at the patient plane 18. The combined radiation field can be characterized by several distributions of bremsstrahlung and scattered photons. All of these distributions must be understood in order to develop a useful source algorithm for input into any Monte Carlo dose calculation code.

This method uses a series of correlated histograms to reproduce the phase-space information obtained from full-scale Monte Carlo simulations of accelerator treatment heads. Errors in the total energy fluence at the isocenter, when compared to that given by the underlying full-physics Monte Carlo simulation, are below 1% of the maximum energy fluence in the region of illumination. Errors for the photon energy fluence arising from any one hardware component, e.g., the target or the flattening filter, are kept well below this criterion of 1% of the maximum energy fluence in the region of illumination.

The algorithm's computational efficiency has two bases. The first is conceptual: the algorithm is designed to generate only photons which have a high probability of going through the aperture defined by the jaws. Little time is spent generating photons that will not reach the patient. The second basis is the use of alias-sampling techniques which allow the use of finely-binned distributions without a corresponding increase in the run-time of the code.

The correlated histograms used by this algorithm may be generated automatically (i.e., without user intervention) from the data files resulting from the Monte Carlo simulation of the accelerator head.

This disclosure deals with photons emanating from the accelerator head. Note that these photons, once generated, must next be transported through any patient-dependent beam modifiers as well as through the air column above the patient.

Methods and Materials

Use of Monte Carlo radiation transport simulation codes to study the output of accelerator heads is well established. A schematic of the modeling process is shown in FIG. 1. Electrons with kinetic energies at or near the nominal operating energy are incident on a target material at the top of the accelerator head. The resulting bremsstrahlung photons are tracked through the accelerator head. Secondary photons and electrons produced within the accelerator head are also tracked. Particles arriving at the bottom of the head are tallied. A "tally" consists of recording the particle's phase-space information (position, direction, energy, particle type), its Monte Carlo weight (accounting for the various physics-biasing schemes used), and any additional information desired about the particle. This might include where the particle was last scattered, the type of scattering event, how many scattering events it underwent, etc.

The simulations described herein were performed using the Monte Carlo codes BEAM96 and MCNP4B based on machine drawings and materials data supplied by the accelerator manufacturers. (For the purposes of this disclosure, patches were applied to the "as-released" MCNP4B to include "BEAM-style" LATCH capability and to use BEAM-style bremsstrahlung splitting). Approximately $5 \times 10^6$ to $2 \times 10^7$ incident electrons are used in the simulations, depending on which accelerator is being modeled. (To date we have simulated eight accelerators made by Varian, Inc. These are the 600C: 4Mv and 6MV, 600CD: 6MV, 2100C: 6MV, 8MV, 10MV, 15MV, and 18MV). Given the variance reduction schemes used (e.g., forced collisions, particle splitting), the resulting phase-space files contain information for $\sim 3 \times 10^7$ photons (of varying weights) and occupy ~1 GB to ~3 GB each, depending on the code used to generate the files.

Unless otherwise specified, the plots shown in this disclosure are all based on a 6MV Varian 2100C data set calculated with BEAM96.

Analysis and Algorithm Development

Figure 2:
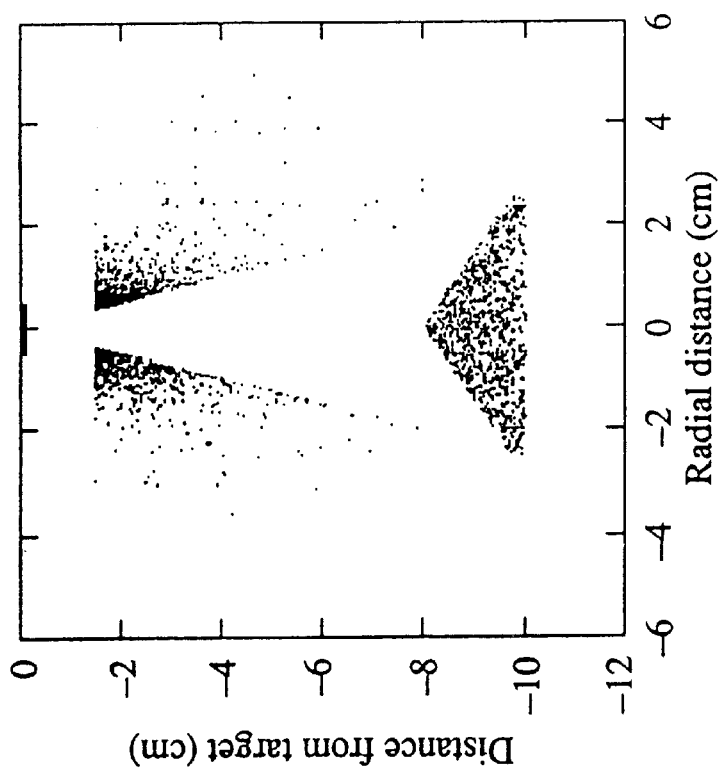
FIG. 2 shows how backtracking of the photons to their point of origin indicates which portions of the accelerator head contribute to the output energy fluence.

Preliminary Analysis of Phase-Space Files Resulting from Monte Carlo Simulation of Treatment Heads The initial check of the photon phase-space file involves graphing the place of creation (or of last scattering) ($x_c$, $y_c$, $z_c$) of the first ~$10^5$ photons in the file. Such a scatter plot of $x_c$ vs $z_c$ for a stylized (fictitious) accelerator head is shown in FIG. 2. This step in the phase-space analysis serves two purposes—the first being practical, the second being conceptual. First, it is a useful check on the input to the program, since the locations of the photon creations should correlate with the physical structure of the accelerator head; and second, it shows which portions of the treatment machine head contribute to the output of the machine. For the example shown in FIG. 2, photons originating from the target "target photons") come from a well-defined spot. Photons coming from the primary collimator ("primary collimator photons") are fewer in number, and they tend to come from the upper edge of the collimator. Thus, the inner surface of the primary collimator is not a uniform source of photons. Rather, the primary collimator appears to be more of a "ring" source. The flattening filter is also a source of photons ("flattening filter photons"). Unlike the primary collimator, however, where the photons originate in only a small fraction of the collimator, photons originate in the entire volume of the flattening filter.

Figure 3:
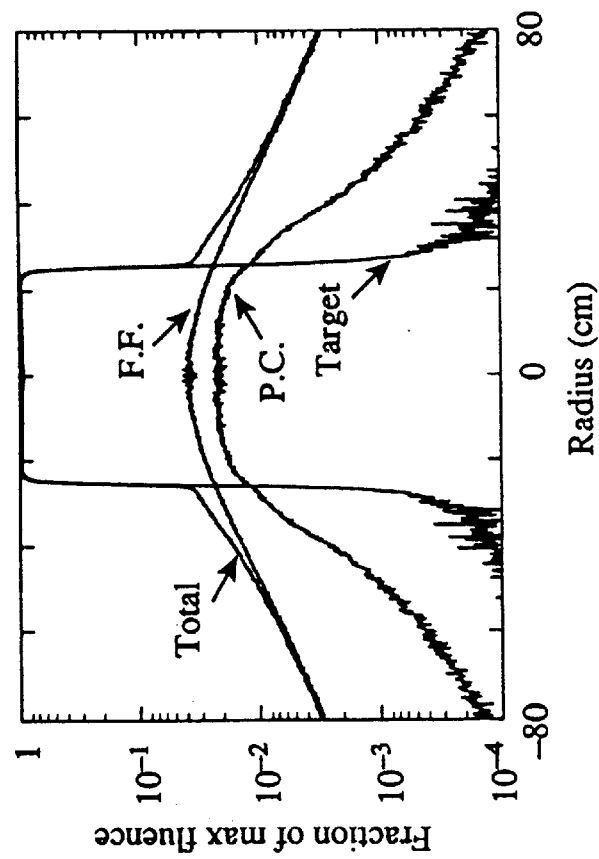
FIG. 3 shows energy fluence distributions from a Varian 6MV accelerator.

The energy fluence distributions at the isocenter plane are shown in FIG. 3. Most of the energy comes directly from the target, with contributions at the several percent level from the flattening filter and the primary collimator. This gives a more quantitative description of the relative importances of the treatment machine head components. The energy fractions coming from each treatment head component and the physics mechanisms involved are given in Table I. Bremsstrahlung is the dominant production mechanism of target photons; incoherent scattering produces most of the photon energy from the primary collimator and flattening filter.

TABLE 1

| Production MECHANISM | HARDWARE | | | |
|---|---|---|---|---|
| | TARGET + TARGET BACKING | PRIMARY COLLIMATOR | FLATTENING FILTER | TOTAL |
| BREMSSTRAHLUNG | 0.9045 | 0.0004 | 0.0003 | 0.9052 |
| INCOHERENT SCATTERING | 0.0238 | 0.0247 | 0.0376 | 0.0861 |
| COHERENT SCATTERING | 0.0030 | 0.0014 | 0.0034 | 0.0079 |
| POSITRON ANNIHILATION | 0.0004 | 0.0002 | 0.0001 | 0.0007 |
| TOTAL | 0.9318 | 0.0266 | 0.0415 | — |

Illumination Regions at the Isocenter Plane

Next the regions on the patient plane that are illuminated by photons from the electron target, the primary collimator, and flattening filter are established.

Target Photons

FIG. 3 shows that the energy fluence for target photons decreases quite rapidly at approximately 25 cm from the central axis. The spatial extent of the energy fluence of target photons is limited by the opening angle of the primary collimator. Beyond 29 cm from the central axis, the energy fluence curve for the target photons has decreased to below 0.3% of its maximum value. Based on the accuracy requirement of <1% given in the above, 29 cm from the central axis is the maximum radius that needs to be considered "reachable" by photons from the bremsstrahlung target.

Primary Collimator and Flattening Filter Photons

FIG. 3 shows that photons from the primary collimator and flattening filter would, in the absence of the collimating jaws, illuminate very large areas of the isocenter plane. As is shown below, however, the jaws define the maximum area illuminated by these photons.

Figure 4D:
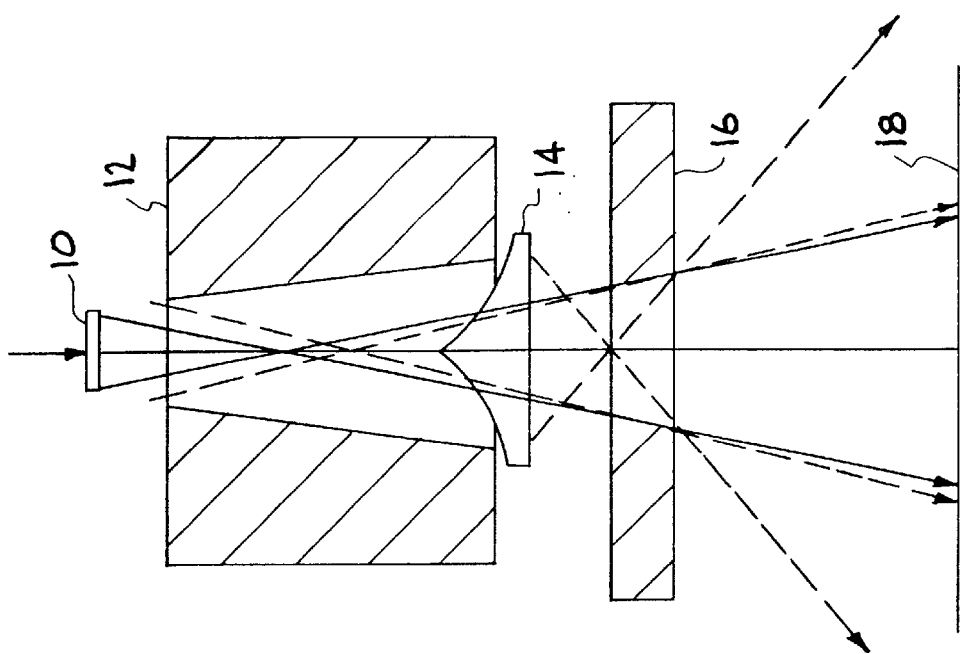
FIGS. 4A–D shows the diameters of the subsources and their relative positions with respect to the jaw opening lead to different areas of illumination at the isocenter plane.
Figure 4A:
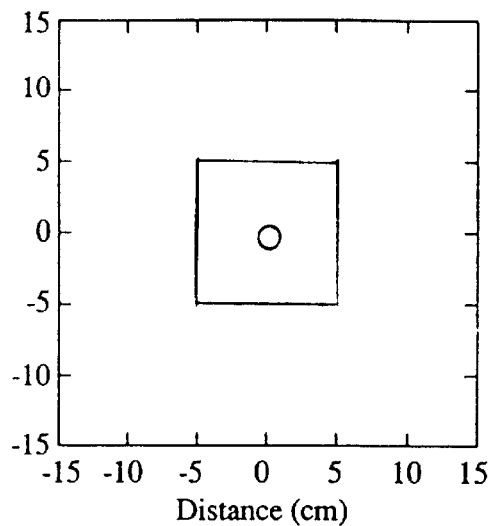
Figure 4B:
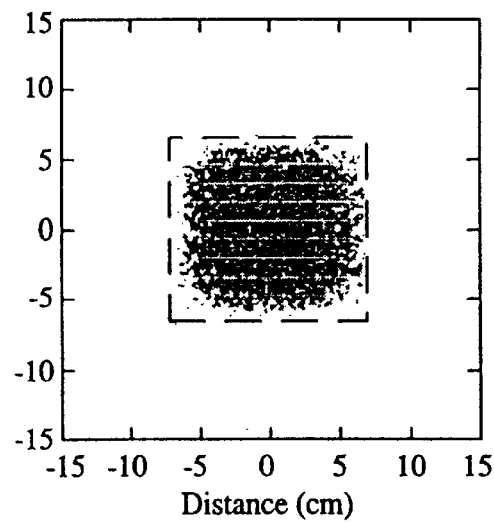
Figure 4C:
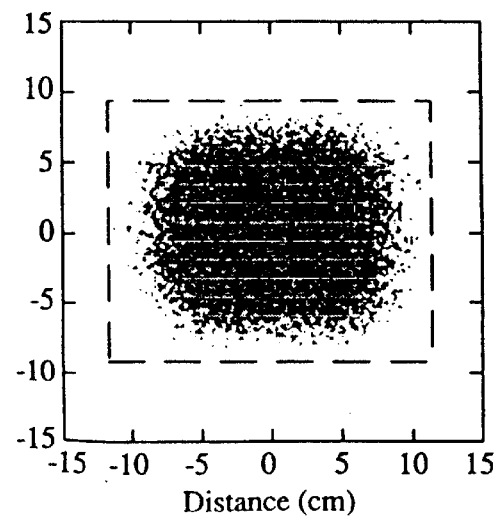
Figure 5A:
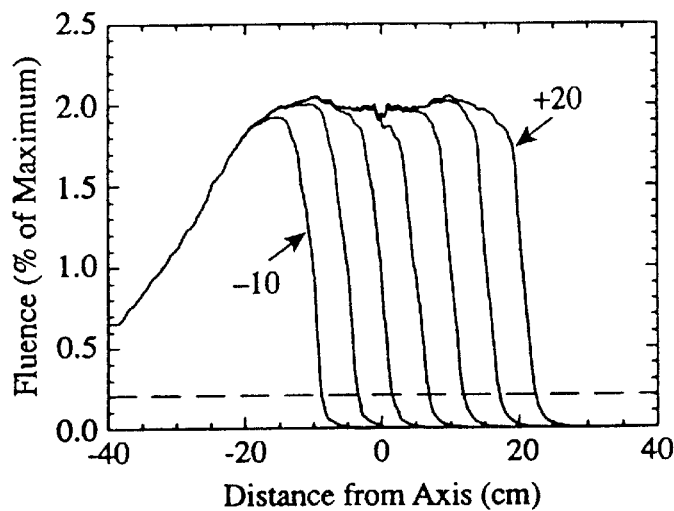
FIGS. 5A–D show the effect of jaw position on energy fluence from the primary collimator and the flattening filter.
Figure 5B:
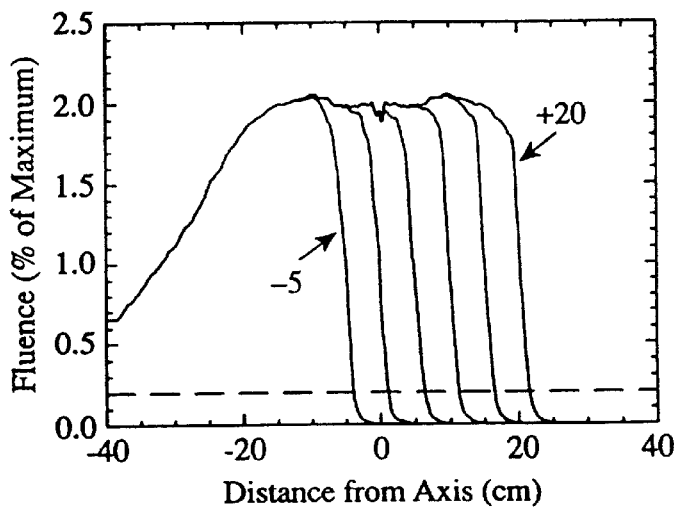
Figure 5C:
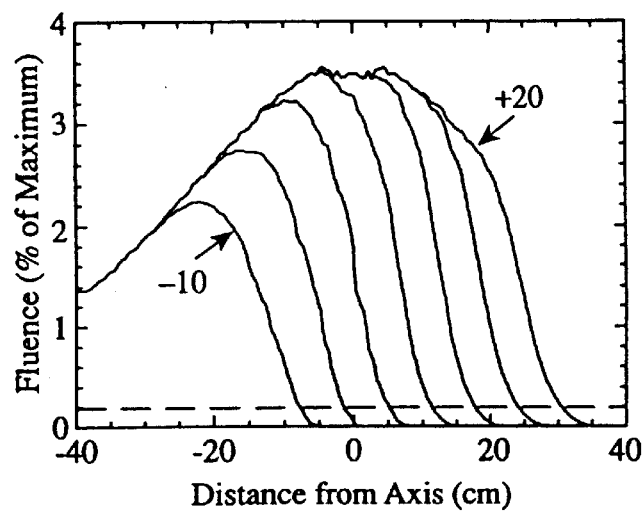
Figure 5D:
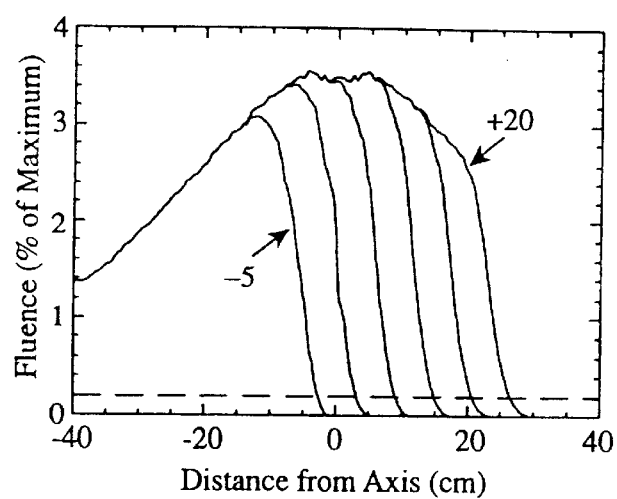

FIGS. 4A–4C show, for a 10 cm×10 cm open field, photons originating in different components of the accelerator head ("subsources") illuminate different but distinct regions of the isocenter plane. It should be understood that many other subsources may be used, depending upon the type of accelerator head used. As shown in FIG. 2, target photons (FIG. 4A) originate in a small (~2 mm diameter) area, well removed from the jaws. Primary collimator photons (FIG. 4B) originate in a slightly larger source, (~1.5 cm diameter) area which is slightly closer to the jaws. Finally, flattening filter photons (FIG. 4C) originate in an even larger (~3 cm diameter) area which is fairly close to the jaws. FIGS. 4D includes a schematic that shows that this difference in vertical location leads to different, but still distinct areas of illumination at the isocenter plane. The positions of the edges of these areas are due to the relative locations of the treatment head components and the movable jaws. The positions of these edges move as each jaw moves. The upper jaws give slightly different edge positions than do the lower jaws because of the difference in vertical position variation of edge position as the jaw position is varied as shown in FIGS. 5A–D for both the primary collimator and the flattening filter. (These figures were generated by reading the photon trajectories from the phase-space file for this accelerator and seeing if the trajectory would intersect a jaw. The jaws were assumed to be infinitely attenuating.) The blocking effect of the jaw is clearly visible for each jaw position.

Radial Tracking Cutoffs

In keeping with the stated goal of keeping errors in energy fluence to below ~1% of the maximum energy fluence, it is arbitrarily declared that a subsource only illuminates those areas where it contributes more than 0.2% of the maximum in-field energy fluence. This level thus defines the edges of the field beyond which Monte Carlo tracking of photons from the given subsource will not be performed. This 0.2% cut-off level is indicated by the dashed lines in each panel of FIGS. 5A–D. The resulting field-size limits are tabulated in Table II.

TABLE II

| JAW SETTING | PRIMARY COLLIMATOR | | FLATTENING FILTER | |
|---|---|---|---|---|
| | UPPER | LOWER | Upper | LOWER |
| +20 | 22.6 | 21.7 | 30.5 | 26.6 |
| +15 | 17.3 | 16.6 | 24.1 | 20.8 |
| +10 | 12.0 | 11.4 | 17.7 | 15.0 |
| +5 | 7.0 | 6.4 | 11.4 | 9.2 |
| 0 | 1.7 | 1.2 | 5.2 | 3.2 |
| −5 | −3.3 | −3.9 | −1.5 | −2.7 |
| −10 | −8.7 | — | −7.9 | — |

Table II and FIG. 5 show that when the jaws are moved to their maximum extent—corresponding to a 40×40 cm² field—no photons from the primary collimator will be tracked more than $\sqrt{22.6^2+21.7^2}\approx 31.3$ cm from the beam axis on the isocenter plane. Similarly, at this same field size, no photons from the flattening filter will be tracked more than $\sqrt{30.5^2+26.6^2}\approx 40.5$ cm from the beam axis on the isocenter plane. This defines the maximum radii at which the photon output from these components will be characterized.

Application to a Source Algorithm

The tabulated extents of illumination listed in Table II may be used in a source algorithm to sample x and y on the isocenter plane. For the case of a symmetric 10 cm×10 cm field (i.e., all jaws moved to their respective +5 cm setting), primary collimator photons illuminate a $\mp 7.0$ x$\mp 6.4 \approx 180$ cm$^2$ area. Similarly, for this same 10×10 cm field, photons from the flattening filter illuminate a $\mp 11.4$ x$\mp 9.2 \approx 420$ cm$^2$ area. This same analysis may be applied to fields that are asymmetric in x or y (or both). Specifying the field size to be used in a given treatment determines the jaw positions, and these in turn—via FIG. 5 and Table II—determine the minimum and maximum x and y positions for sampling photon positions at the isocenter plane. In addition, using the information in Table II to select a photon's (x,y) position on the isocenter plane ensures, a priori, a high probability that the photon will reach the patient without intersecting a jaw.

Energy Distributions

Figure 6A:
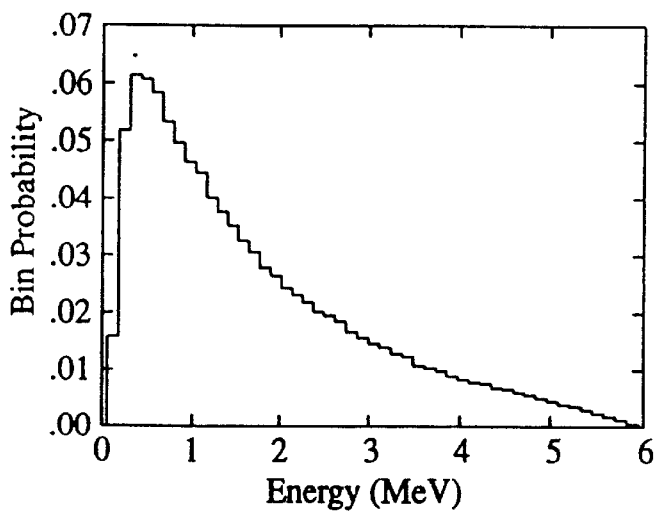
FIGS. 6A–6F shows that the on-axis photon energy distributions depend strongly upon the treatment head component in which the photons are created and the energy distributions at the isocenter plane of these subsources at a distance of 20 cm from the central axis of the accelerator.
Figure 6B:
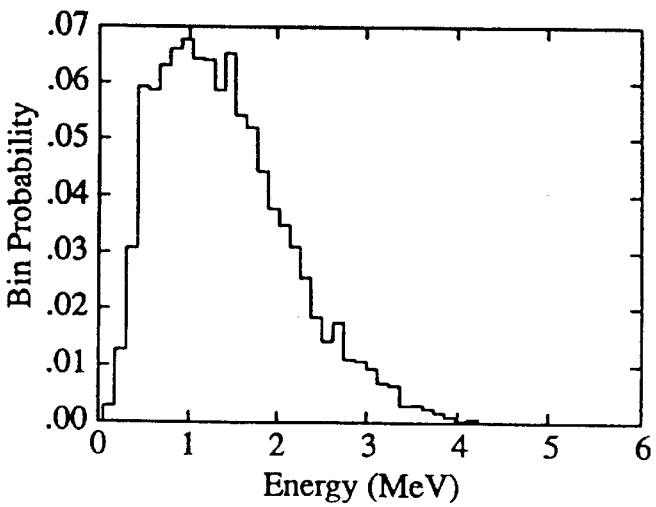
Figure 6C:
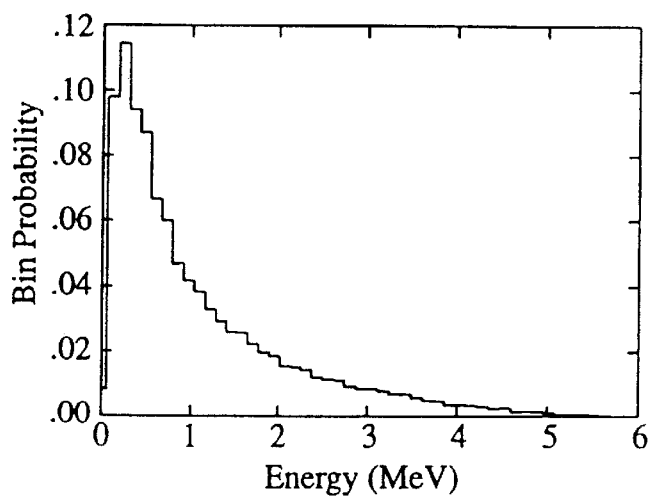

Photon energy distributions of the various components, as tallied at the isocenter plane and on the central axis of the beam, are shown in FIGS. 6A–C. The photon energy distributions vary strongly with the treatment head component in which they are created. Photons from the target have energies ranging from the energy of the initial incident electrons down to low, but not quite zero, energy. This is consistent with the flattening filter's removal of the lower energy photons. The energy distribution from the primary collimator reflects both this filtering process (on the low energy side) and the fact that the photons are Compton scattered through a large angle (thus setting an upper bound on the high energy side). The photon distribution from the flattening filter reflects both the lack of low-energy filtering (since this is the last treatment machine head component transited by the photons) as well as the possibility for small angle scattering (and consequently little energy loss) of the high energy photons coming from the target.

Figure 6D:
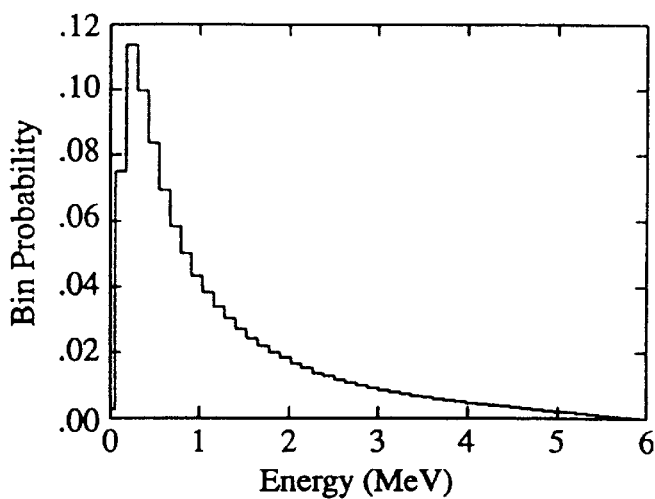
Figure 6E:
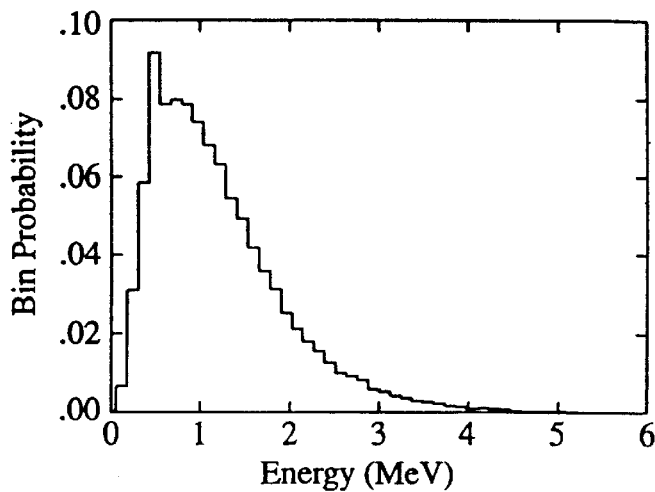
Figure 6F:
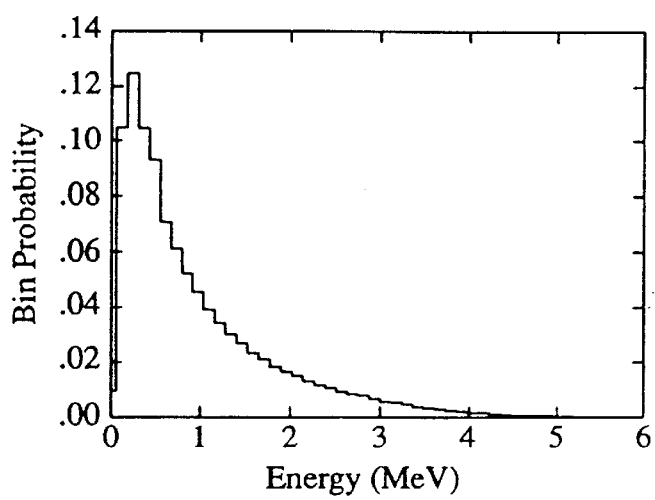

The photon energy distributions vary with the distance from the central axis of the beam. This is shown in FIGS. 6D–6F which shows the distributions as tallied at the isocenter plane and at 20 cm from the central axis of the beam. The distributions for all three subsources show an increase in the proportion of low energy (here, ~1 MeV) photons with increasing distance from the central axis, which correlates with the decrease in the thickness of the flattening filter traversed by these photons.

Photon Origin Distributions

The subsources, in addition to illuminating different size areas of the patient, also have markedly different source distributions. The target photon source is a flat disk, the primary collimator photons come from a ring-like source, and the flattening filter photons come from a broad and centrally-peaked source.

While these distributions are quite different, each may be accurately described by a radial distribution and an angular distribution, as discussed below.

Target Photons

Figure 7A:
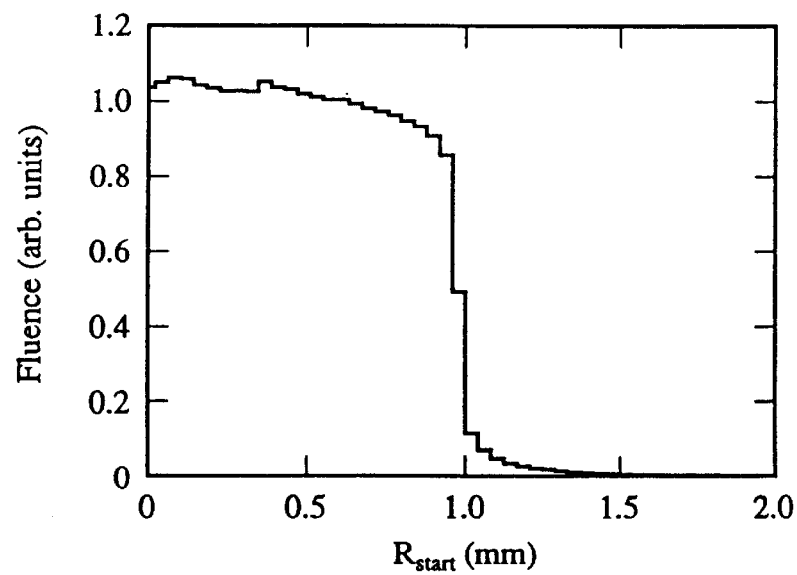
FIGS. 7A and 7B show closeup views of the probability distribution for photons from the target.
Figure 7B:
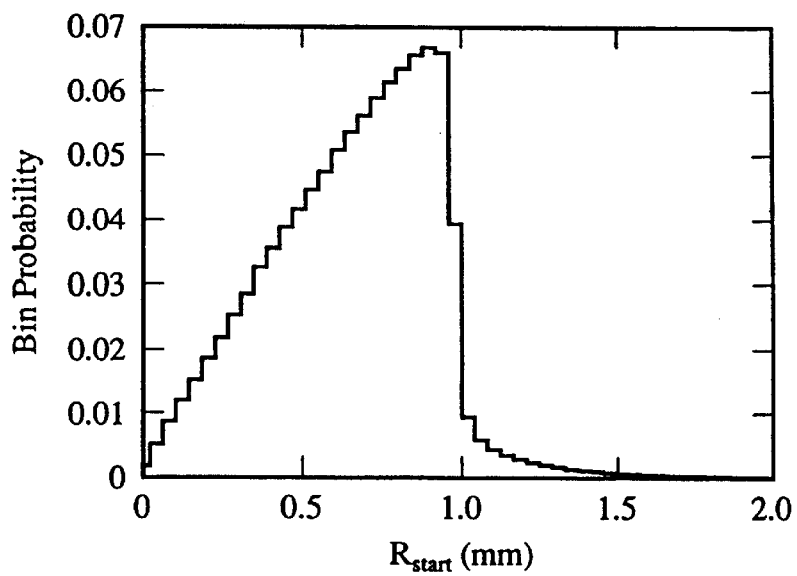

Target photons come from a well-defined disk whose radius matches that of the incident electron beam. A cross section through the spot is shown in FIGS. 7A and 7B. The source distribution is relatively flat. There is also a low-intensity tail at larger R, due to those photons which scatter within the target before heading towards the patient. (The photons in the target which are scattered outside of the electron beam have low energy, and strictly speaking should not be combined with the photons created within the radius defined by the electron beam. Given the small radial extent of the tail, in practice we treat target photons as coming from one source.) The energy fluence plot shown in FIG. 7A is equivalently expressed as the radial-probability function shown in FIG. 7B. The azimuthal distribution of target photons is uniform. For this reason, a uniformly distributed (cos $\Phi$, sin $\Phi$) pair is genereteed and then obtain:

$$(x_{start}, y_{start})=R_{start} (\cos \Phi, \sin \Phi). \qquad (1)$$

Scattered Photons

Scattered photons are handled in a fashion similar to the photons from the target, in that the source position is obtained from an ($R_{start}$, $\Phi_{start}$) pair. The difference here is that $\Phi_{start}$ is also chosen from a distribution, instead of being chosen uniformly on the interval (0,2π).

Figure 8B:
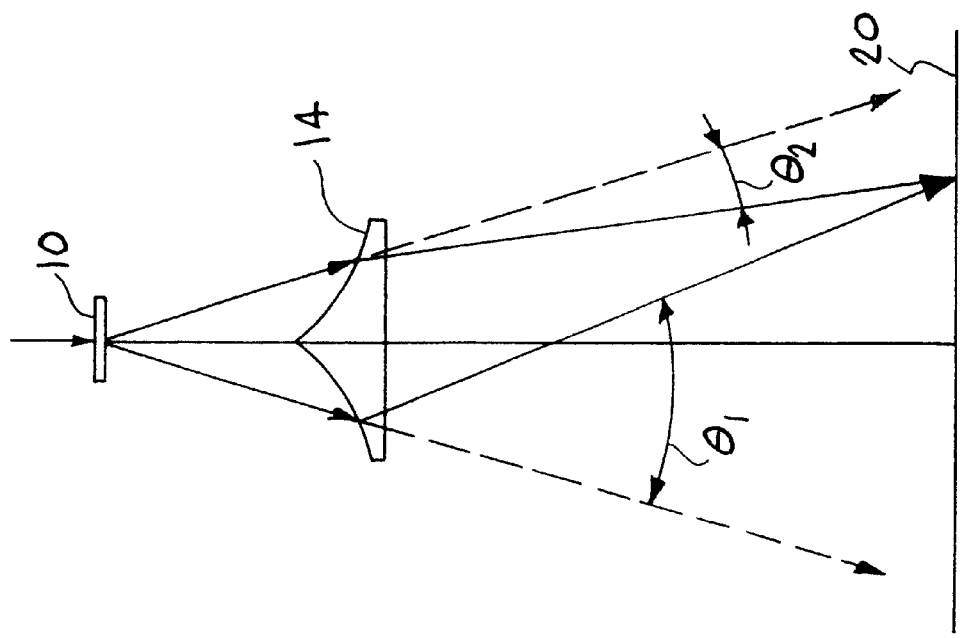
FIGS. 8A–8C show the effect of source position on photon enery.
Figure 8A:
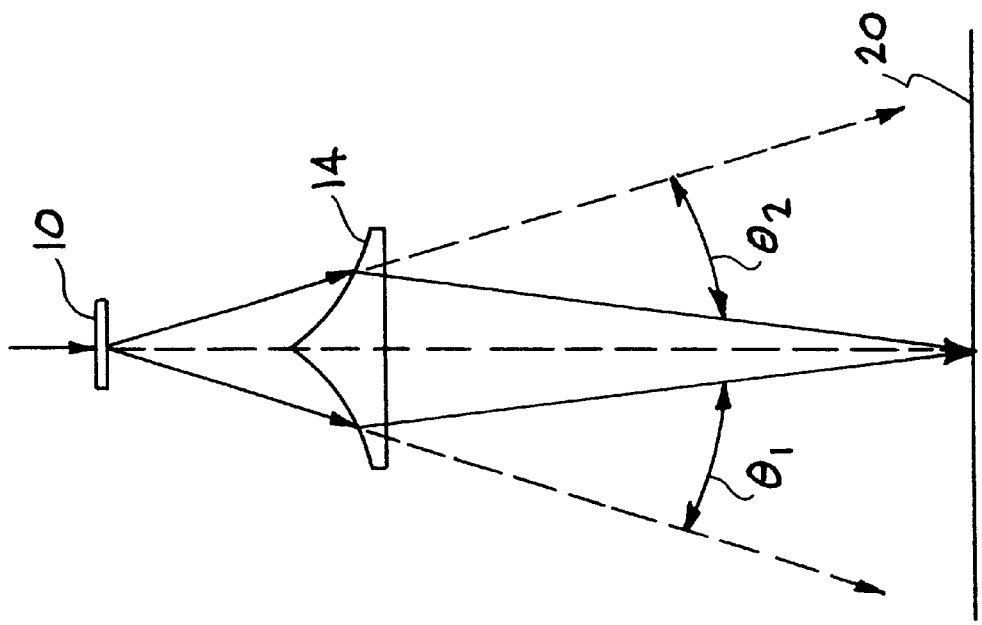

The motivation for using an angular distribution is given in Table I and FIGS. 8A and 8B. At any point on the isocenter plane 20 not on the symmetry axis of the machine, there is a distinct difference in the scattering angle for events occurring at the "near" edge and the "far" edge of the scatterer, whether it be the flattening filter as shown in the figures or the primary collimator. Calculations indicate that incoherent scattering is the dominant production mechanism for photons in both the primary collimator and the flattening filter (Table I). Since the energy of the scattered photon varies inversely with the scattering angle, more photon energy will come from the "near" portion of the treatment head component.

Figure 8C:
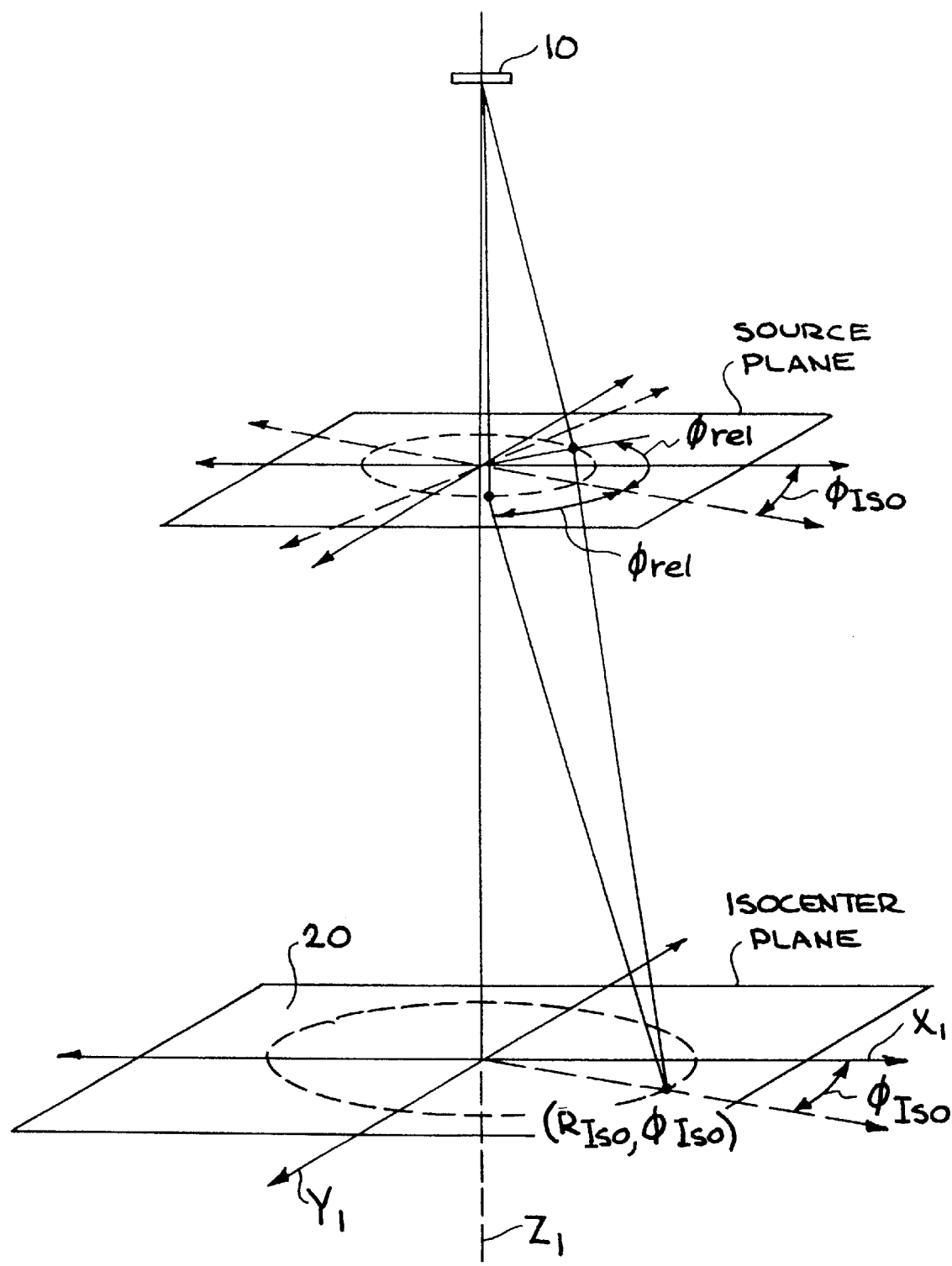
Figure 11A:
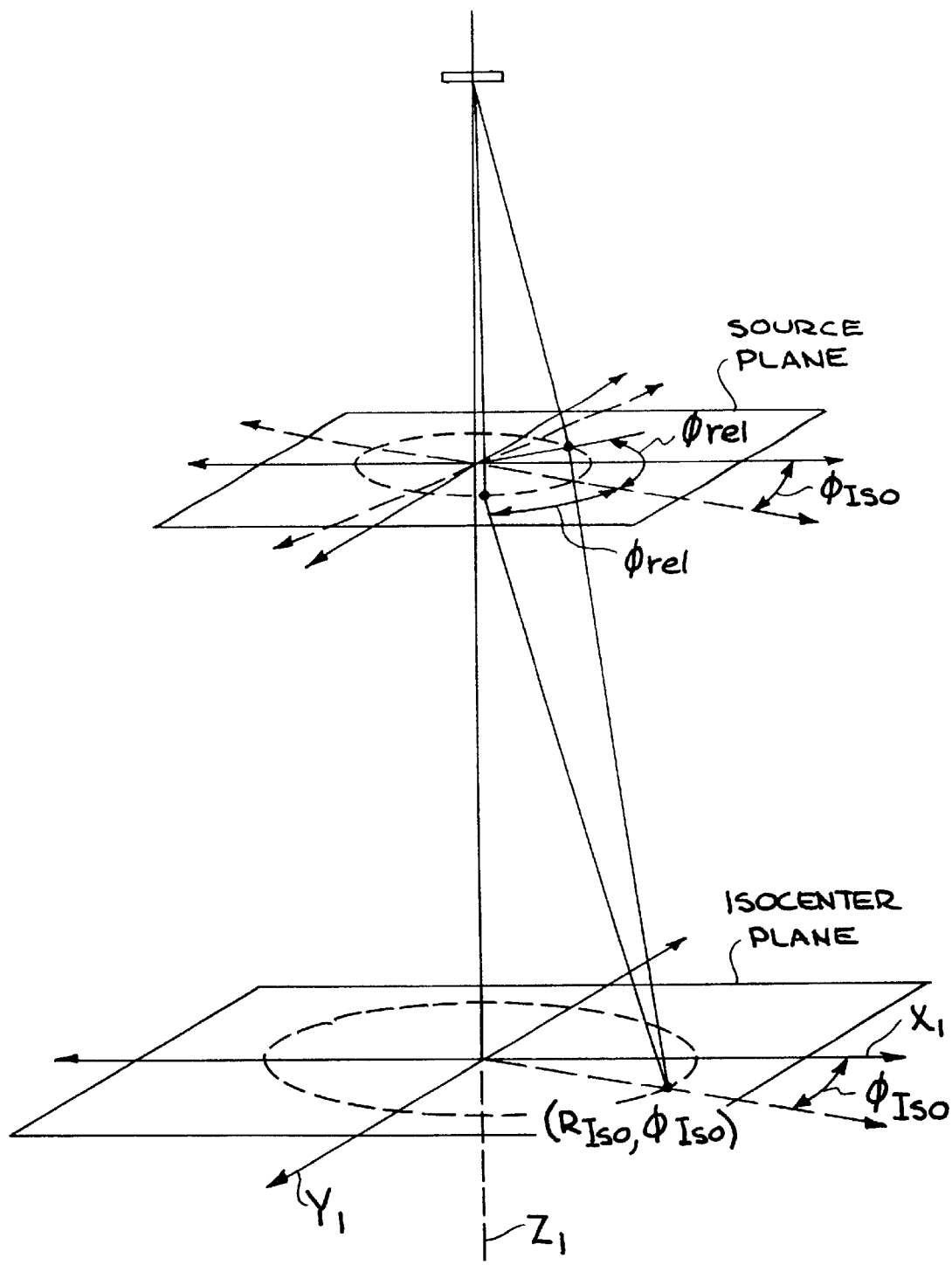
FIGS. 11A–F, a modified form of FIG. 8, show the correlated histograms used to describe the subsources constituting a treatment machine.
Figure 11:
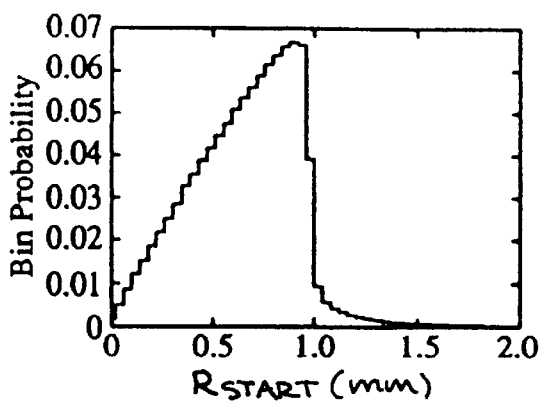
Figure 11:
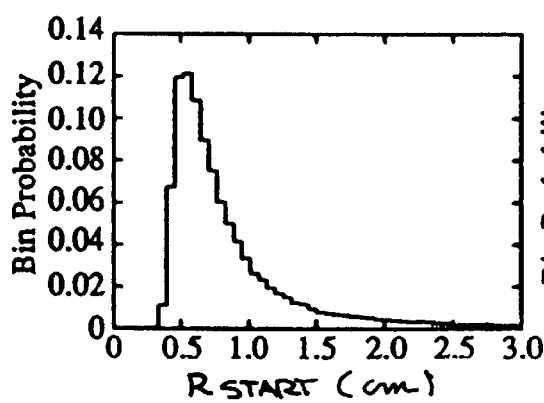
Figure 11:
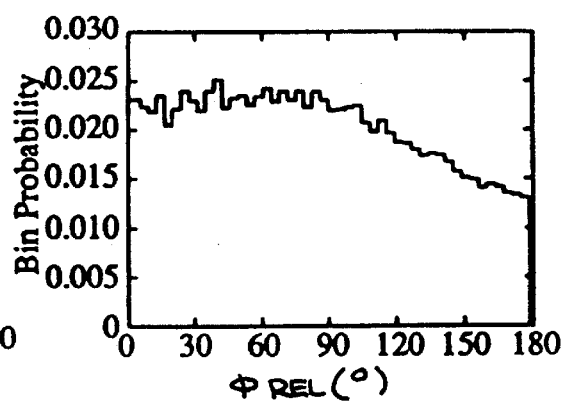
Figure 11:
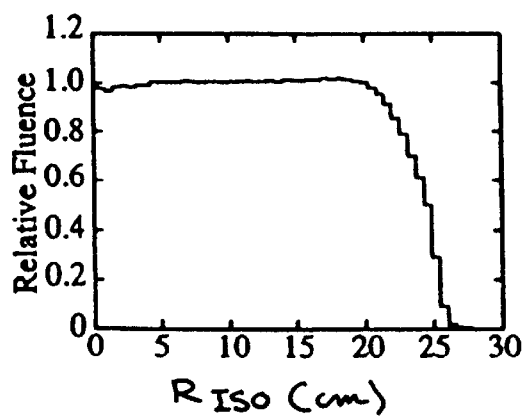
Figure 11:
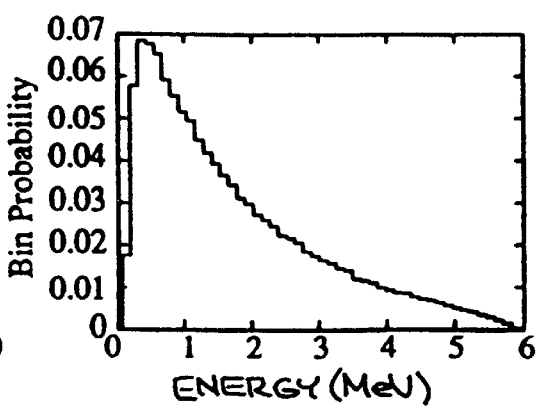

This leads us to the coordinate system used to describe the starting position of a photon trajectory. As shown in FIG. 8C, a polar coordinate system may be defined at the position of the source plane of the particles. The angular origin of this system may be defined by the plane containing the beam axis and the photon's position of intersection at the isocenter plane. This yields a simple decomposition of the starting position in terms of relative azimuthal angle $\phi_{rel}$, where $\phi_{rel}$ ranges from the value of 0° for the "near" edge to the value, given the reflection symmetry involved, of 180° for the "far" edge of the scatterer.

Primary Collimator

The source is fairly isotropic for small radii. This isotropy disappears off-axis, with the distribution in the last panel showing the effect of moving beyond the collimator angle: the "near" edge is blocked and only photons from the back surface of the collimator can reach the isocenter plane (FIGS. 9A–9F).

Flattening Filter

This same effect appears in the case of the flattening filter. Here, too, the source distributions favor the "near" edge of the flattening filter. The azimuthal anisotropy increases with increasing $R_{Iso}$ (FIGS. 10A–10F).

Sampling Algorithm

Overview

Turning now to the development of a source algorithm for a Monte Carlo photon teletherapy code. The "source problem," as described above, was to be able to generate photons in a manner that was both accurate and efficient. Two general patterns are seen to emerge during the preceding discussions. The first trend is that the energy spectra, radial energy fluence variations, and starting distributions differ strongly for different subsources. Second, for a given subsource, the energy distributions, the radial energy fluence, and the starting distributions all vary smoothly and relatively slowly as a function of the photon's radial position at the isocenter plane.

Separate the overall photon phase-space into individual phase-spaces, each designated by the treatment-head component in which the photons originate. Next subdivide the phase-space of each subsource into "tiles": equal-width annular regions defined at the isocenter plane. It was shown above that given the maximum ranges of travel of the collimating jaws—the maximum distance from the central axis at which a photon has a significant probability of landing is ~29 cm for target photons, ~31 cm for primary collimator photons, and ~41 cm for flattening filter photons. Currently ten tiles are used for each subsource. Each tile has its own photon energy spectrum; the radially slowly-varying energy spectrum of the subsource appears as a tile-dependent energy spectrum. In addition to its energy spectrum, each tile has its own $R_{start}$ and $\Phi_{rel}$ distributions to describe photon starting positions.

Implementation

The correlated histograms used to describe the photon phase space are shown in FIGS. 11A–11F. Consider the problem for a treatment consisting of one field size for one machine; the generalization to multiple field sizes is straightforward. The use of the correlated histograms in calculating a treatment plan requires several preprocessing steps, in addition to the steps performed at runtime:

(1) Preprocessing steps:
(a) read the data file(s) for the machine(s) used in the calculation;
(b) convert each of the energy, angle, and radial probability histograms into the form required for alias sampling;
(c) use the jaw positions specified in the treatment plan to determine the limits of the ($x_{Iso}$, $y_{Iso}$) sampling areas for each subsource of each beam;
(d) for each subsource, use the ($x_{Iso}$, $y_{Iso}$) sampling areas to calculate the energy delivered to the isocenter plane; and
(e) use the relative energy contributions as sampling probabilities for each subsource.

(2) Generating photons during run-time:
(a) use random sampling to determine which type of photon (e.g., target, primary collimator, or flattening filter) will be generated. As indicated in Table I, these photon subsources will be selected with relative probabilities of approximately 93:3:4. The actual relative probabilities will depend on the jaw settings of the particular treatment plan.
(b) for this photon type, and given the jaw settings, look up the x and y limits of illumination (FIG. 4) on the isocenter plane. Generate a random, uniformly distributed ($x_{Iso}$, $y_{Iso}$) coordinate pair within this area.
(c) given this ($x_{Iso}$, $y_{Iso}$) pair, calculate $R_{Iso}$. Adjust the weight of the particle to account for the slowly-varying energy fluence (FIG. 3) of this photon type. Given $R_{Iso}$, determine the tile index. Calculate $\Phi_{Iso}$.
(d) based on the tile index, sample the particle's energy from the energy distribution appropriate for this $R_{Iso}$ (FIG. 6).
(e) sample a starting radius $R_{start}$ from the appropriate distribution;
(f) sample a relative starting angle $\phi_{rel}$. For target photons, use Eq. (1).

For other photons, sample the appropriate distribution.

The particle's energy and weight have thus been determined (steps c and d), as have two points defining the particle's trajectory (steps b, e, and f). The trajectory-defining points define the particle's direction cosines, and the required phase-space information needed to start tracking this particle is now complete. The photon is backtracked to the bottom of the monitor chamber, and then transported through beam modifiers (if any) to the patient. A PEREGRINE-specified plane is a plane where PEREGRINE starts to track a particle through air towards a patient, wherein the step of calculating the phase-space information for a specific radiation accelerator head from the correlated histograms comprises using the values of $X_{start}$, $Y_{start}$, $Z_{start}$, $X_{Iso}$, $y_{Iso}$ and the known $z_{Iso}$ for a specific accelerator to determine a particle trajectory's intersection with the PEREGRINE-specified plane.

Accuracy

The next question is that of the accuracy of the algorithm described above. Accuracy as defined here refers to the degree to which our algorithm reproduces the underlying photon phase space. This is a two-part question. The first question deals with the energy distribution(s) of the photons at the isocenter plane. The second question deals with the trajectories of the photons.

Energy Distribution at the Isocenter Plane

Figure 12A:
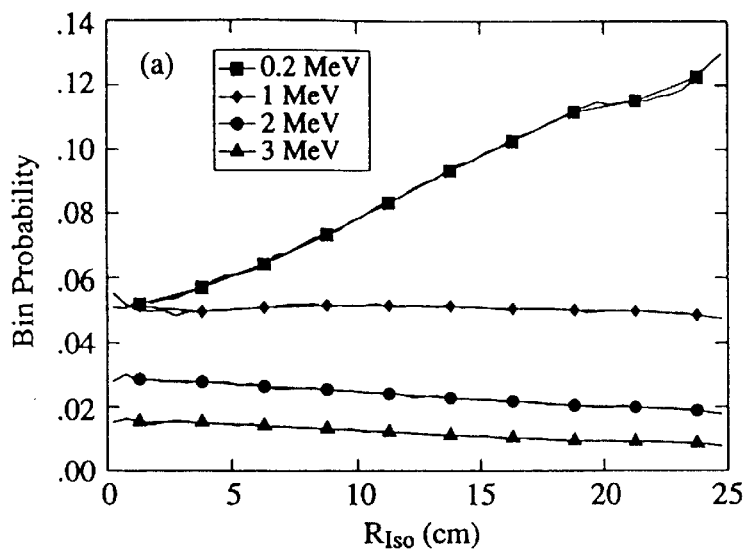
FIGS. 12A–C show radial variations of the heights of the probability bins for several photon energies.
Figure 12B:
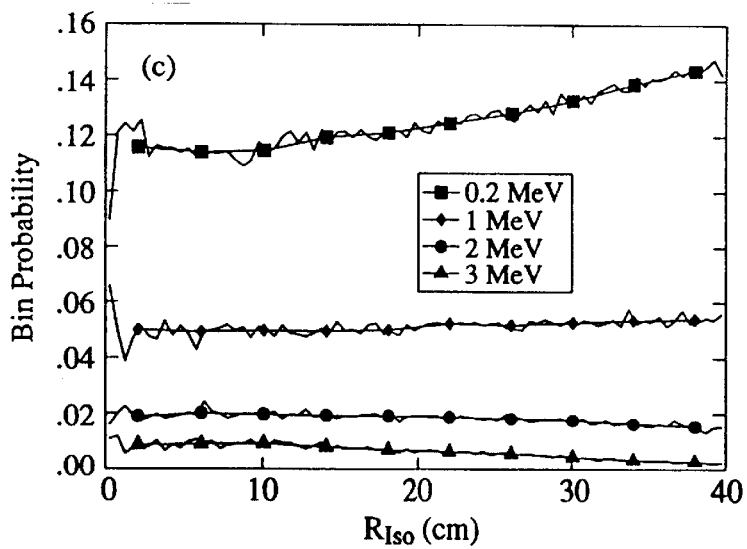
Figure 12C:
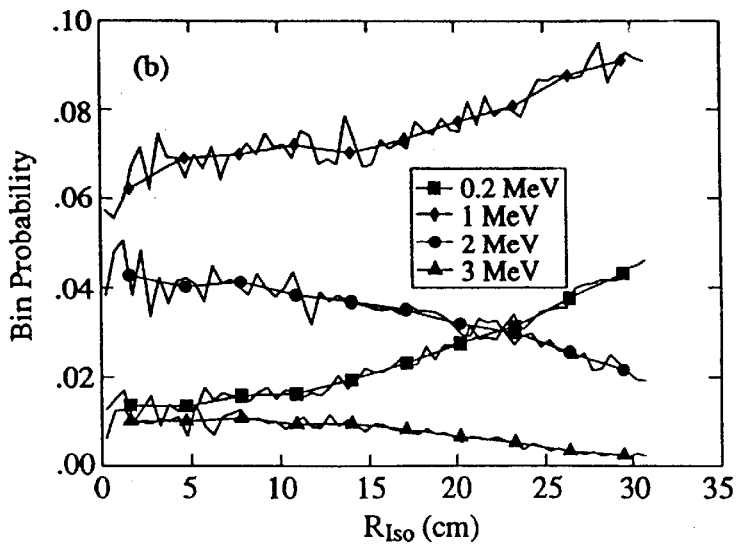
Figure 13:
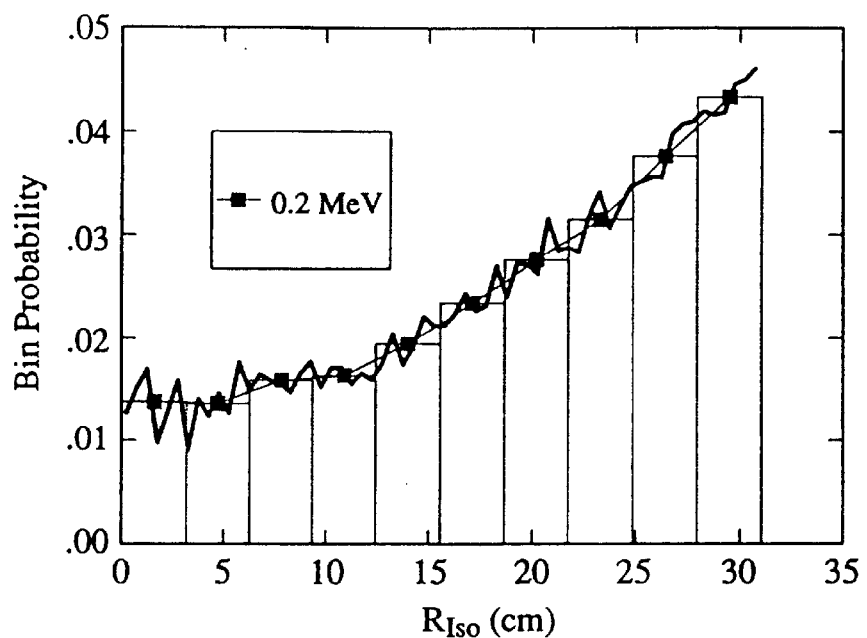
FIG. 13 shows the "knot points" of the piecewise-linear functions shown in FIG. 12 are the bin-centers and bin-heights obtained during histogramming of the raw data.

These distributions are accurately reproduced because (a) the binning of the energy distributions is actually performed at this plane, and (b) because the distributions vary slowly enough with distance from the axis (FIG. 12) that a piecewise-linear distribution can track the change (FIG. 13).

This variation with radial distance is slow. FIGS. 12A–12C show curves of bin probability for several energies are plotted as functions of radius at the isocenter plane. These curves are all slowly varying and are all accurately represented by piecewise-linear functions. In addition, only a small number of pieces—on the order of 10—is sufficient.

Because the knots of the piecewise-linear functions shown in FIG. 12 are actually the bin-centers of histograms obtained by binning the photon energies over this range (FIG. 13), the radial variation in the energy distribution over the area of interest may be reproduced by creating energy histograms in a small number of annular regions (the "tiles") at the isocenter plane. A photon energy distribution of the form shown in FIG. 6 is then created within each tile. The maximum tile radius is determined by the maximum radius of interest for the particular photon distribution. For the photons coming from the bremsstrahlung target, the maximum radius is ~29 cm. Similarly, as noted above, for the primary collimator and flattening filter, maximum tile radii of 33.6 and 40 cm are required.

Trajectory Information

The second question deals with the trajectories of the photons. Our source algorithm determines the trajectory of the photons by "connecting the dots," one of which is at the isocenter plane and the other of which is either at or within a few centimeters of the position of the bremsstrahlung target. The radial extent of the source distributions is on the order of 1 mm for the target photons, and on the order of 1 cm to 3 cm for photons scattered from the primary collimator or the flattening filter. The maximum expected trajectory error, therefore is expected to be no larger than $\delta\theta \approx \arctan 3/100 \approx 2$ deg. The actual error will be smaller because of the use of the starting R and $\Phi$ distributions.

Figure 14:
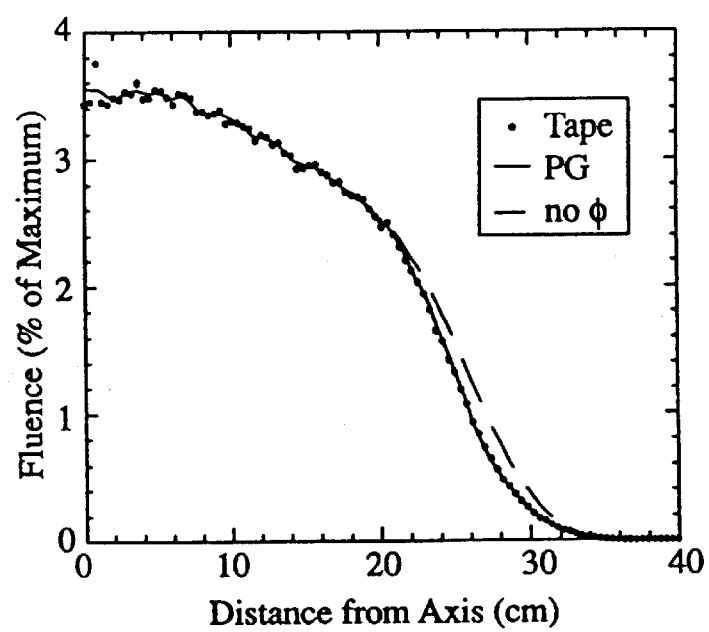
FIG. 14 shows roll-off in photon energy fluence for flattening filter photons, at field edge defined by upper jaw at the position for a 40×40 field.

The accuracy of the trajectories may be checked by comparing the location and width of the jaw-edge penumbra for each source as a function of jaw position with the location and width obtained with the underlying phase-space file (a "knife-edge" test). While the position of the photon on the isocenter plane is selected at random, an "error" in the photon's direction cosines will cause an error in its assumed trajectory. This trajectory error would affect, for example, whether or not a photon near the edge of a treatment field would be blocked by a jaw edge. This type of test is shown in FIG. 14 for flattening filter photons, with the upper jaw moved to its maximum distance from the centerline of the beam. The roll-off in energy fluence is well-matched by the source algorithm presented in this paper, indicating that the use of correlated R and $\phi$ distributions accurately reproduces the photons' trajectories. FIG. 14 also shows the fluence error that results when $\phi$ is assumed to be uniformly distributed.

Computational Efficiency

This algorithm's computational efficiency has two bases. The first of these is the conceptual structure, in which we first pick only those photon trajectories that enter that portion of the isocenter plane which is illuminated for the specified jaw settings. Only then do we generate a starting position to determine "where they came from." The second basis is the efficiency of the "alias method" (see below) to sample the various probability distributions used to describe the photon phase space. This method requires two random numbers to select a bin from a distribution of arbitrary length and complexity. A third random number is required if uniform sampling within the bin is desired.

The computational burden of the algorithm is detailed in Table III. Note that the source algorithm determines the six needed pieces of the particle phase space information (x, y, u, v, E, q, weight) using approximately 14 random numbers and 3 or 4 table lookups. (Recall that, given the context of the problem, z is the isocenter plane location and w=$\sqrt{1-u^2-v^2}$. Step 1, which uses alias sampling to determine which treatment head component from which machine will be selected, makes the running time of this algorithm independent of the number of beams used in the treatment plan.

TABLE III

| STEP # | OPERATION | # OF RNS REQ'D | # OF HISTOGRAMS SAMPLED |
|---|---|---|---|
| 1 | SELECT WHICH COMPONENT OF WHICH BEAM | 2 | 1[A] |
| 2 | SELECT ($I_{iso}$, $y_{iso}$) ON THE ISOCENTER PLANE, ADJUST PHOTON WEIGHT | 2 | 0 |
| 3 | DETERMINE TITLE INDEX FOR ENERGY DISTRIBUTION | 1[B] | 0 |
| 4 | DETERMINE ENERGY | 3[C] | 1 |
| 5 | DETERMINE STARTING RADIUS $R_{START}$ | 3[C] | 1 |
| 6 | DETERMINE STARTING ANGLE $\Phi_{START}$ | 2 OR 4[D] | 0 OR 1 |
|  | TOTAL | 13 OR 15 | 3 OR 4 |

Figure 15:
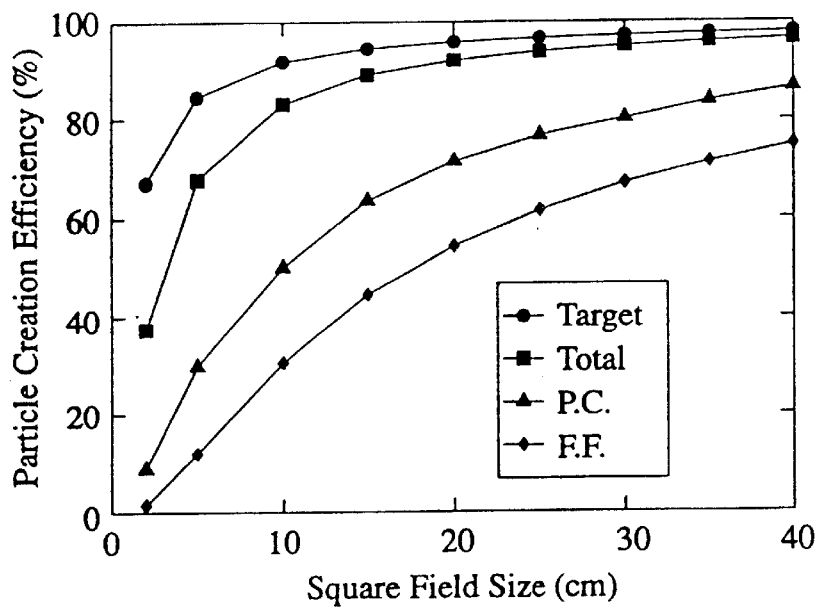
FIG. 15 shows the algorithm generates photon trajectories which may intersect the edges of the jaws

Steps 2 and 6 have the most impact on the algorithm's efficiency. A number of the photon trajectories calculated via steps 2, 4, and 5 will intersect the jaw corners and subsequently not reach the patient. This behavior is intended, since this is how the penumbrae are determined. This effect is most pronounced for small field sizes, and becomes more visible as the radial extent of the treatment head component increases. This is shown in FIG. 15 for a number of square field sizes. For most of the fields, trajectories for "target" photons have a better than 90% chance of clearing the jaws. Photons from the primary collimator and flattening filter have a lower survival probability. Because most of the photons originate in the target, however, the overall efficiency is better than 80% for most fields in the range studied.

Reduction of Phase-Space Files

It was stated above that an automated procedure is useful for converting the gigabyte-sized data files obtained from Monte Carlo simulations of an accelerator head into the correlated histograms described herein. The conversion requires five passes through the 1-GB phase space file and requires approximately 23 minutes to complete. (The computer used is a Digital AlphaServer 8400 Model 5/440 running OSF1 V4.0.)

The five passes perform the following operations:

(1) This step calculates the curves shown in FIG. 5. This step also calculates the data given in Table II. In so doing, the maximum tile radius needed for each subsource, and hence the radial limits of each tile of each subsource are also calculated.

(a) For each particle in the phase-space file:
  (i) read each particle and identify the hardware component in which it last scattered.
  (ii) based on the particle's position at the tally plane ($x_{tally}$, $y_{tally}$, $z_{tally}$) and on the particle's direction cosines (u, v, w), determine where the particle will intersect the isocenter plane. At the same time, determine the jaw settings of Table II for which the particle would miss the jaws. Add this particle to the curves shown in FIG. 5.

(b) At this point, the curves shown in FIG. 5 have been calculated. Each curve is then searched to determine the position at which the height of the curve drops below (the nominal value of) 0.2% of the maximum energy fluence on the isocenter plane.

(c) The location of this crossing point is entered into Table II.

(d) $R_{max}$ is calculated for each subsource, based on the maximum allowed jaw positions, thus determining the radial extent for each tile of each subsource.

(2) This step makes an initial estimate of the position of the "Source Plane" (shown in FIG. 8) for each tile of each subsource. Recall that the source particle algorithm calculates the trajectory of a particle by first choosing a position at the isocenter plane and then asking "where did the particle come from?" Trajectory errors arise because of errors in determining the starting position of a particle. Minimizing the extent of the radial distributions should in turn minimize errors in the trajectories calculated during run-time. To this end, determine the value of z at which each particle comes closest to the central axis of the beam.

(a) For each particle:
  (i) determine its subsource and its tile index;
  (ii) using the particle's position and direction as it intersects the tally plane, trace its path back to where it was closest to the central axis of the beam:

$$Z_{closest} = Z_{tally} - \frac{w(ux_{tally} + uy_{tally})}{1 - w^2}$$

(i) based on this value of $z_{closest}$, add the particle to the appropriate bin of the N(z) histogram for this tile of this subsource.

(b) For each tile of each subsource, set $Z_{guess}$ equal to the value of z at which the N(z) histograms has its maximum value.

Figure 16:
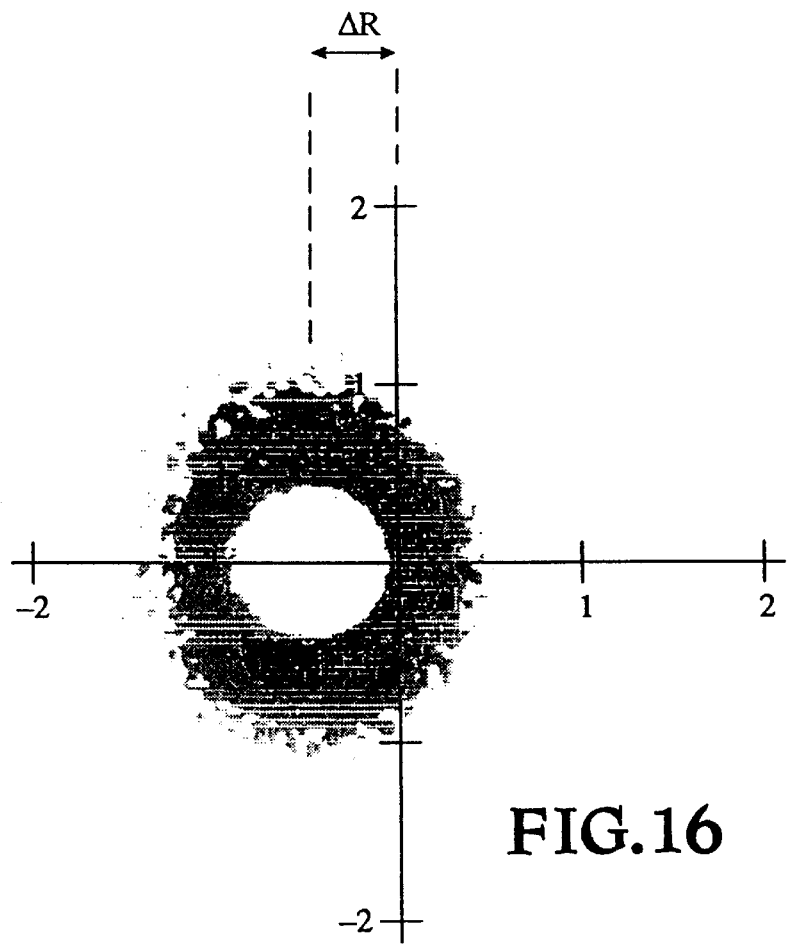
FIG. 16 shows minimizing $R_{closest}$ for most of the particles of an azimuthally-anisotropic subsource leads to an off-center distribution.

(3) This step determines the high-end cutoff value for $R_{start}$ for each tile of each subsource.
  (a) For each particle:
    (i) determine its subsource and its tile index;
    (ii) determine its distance R from the central axis of the beam, at the position $z=z_{guess}$ determined above;
    (iii) add the particle to the appropriate bin of the $R_{start}$ histogram for the appropriate tile and subsource.
  (b) For each tile of each subsource, find the minimum value of R that exceeds Rstart for 99% of the particles.
(4) Fine-tune the $z_{start}$ for each tile of each subsource. The $z_{guess}$ determined by Step 2 above yields a good, but not optimal, value of z at which to create $R_{start}$ and $\phi_{rel}$ distributions. An azimuthally anisotropic starting distribution, shown e.g., for the primary collimator in FIG. 16, appears "off-center" when the photons belonging to this distribution are traced back to $Z_{guess}$. Such a pattern may, however, be searched for that value of ΔR which maximizes the accuracy of a (R, Φ) representation.
  (a) For each particle:
    (i) determine its subsource, tile index, and $z_{guess}$;
    (ii) calculate its (x,y) position at $z_{guess}$; and
    (iii) add the particle to the appropriate bin of a two-dimensional histogram for the appropriate tile and subsource.
  (b) For each two-dimensional histogram so calculated, step along the x axis and at each point:
    (i) assuming this point to be the origin, create an (R, Φ) representation of the (x,y) distribution calculated above;
    (ii) find that value of x, which when used as the origin, minimizes the difference between the (x,y) distribution above and the one calculated from the (R, Φ) representation based on that origin.
  (c) Determine the $z_{start}$ at which no offset-would have been required.
(5) This step creates the correlated histograms needed to describe the accelerator output. For each particle:
  (a) Determine its subsource, tile index, and $\Phi_{Iso}$;
  (b) Determine $R_{start}$ and $\phi_{rel}$ at the $z_{best}$ for this tile and update the appropriate histograms;
  (c) Update the energy distribution of this tile.

The alias sampling method is an efficient method for sampling probability distributions comprising a large number of bins, which in turn may have widely-varying heights. Also, while alias sampling is a very good way to sample distributions, it is not the only method available (other methods are more-easily coded, but tend to be slower). The distributions shown in this typically have both these properties. The alias method has been found to be faster than other methods of sampling distributions, e.g., searching cumulative distributions, while avoiding loss-of-accuracy problems associated with using equal probability distributions.

Figure 17A:
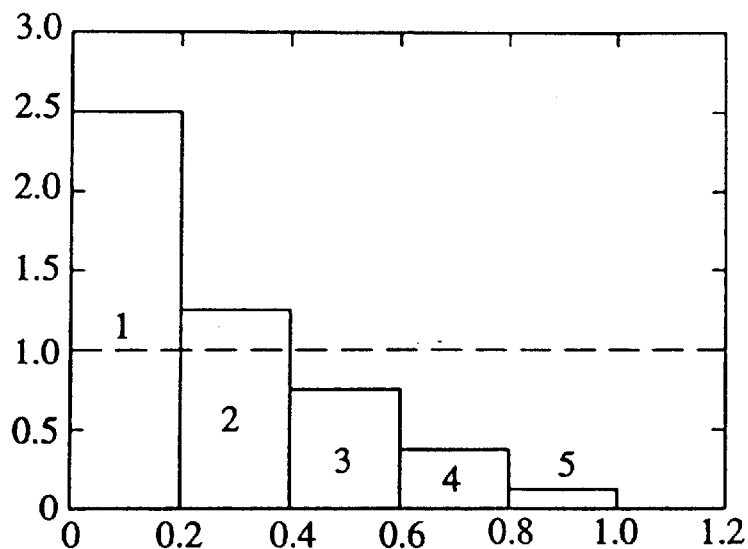
FIGS. 17A and 17B show that the alias sampling technique allows any distribution to be sampled efficiently
Figure 17:
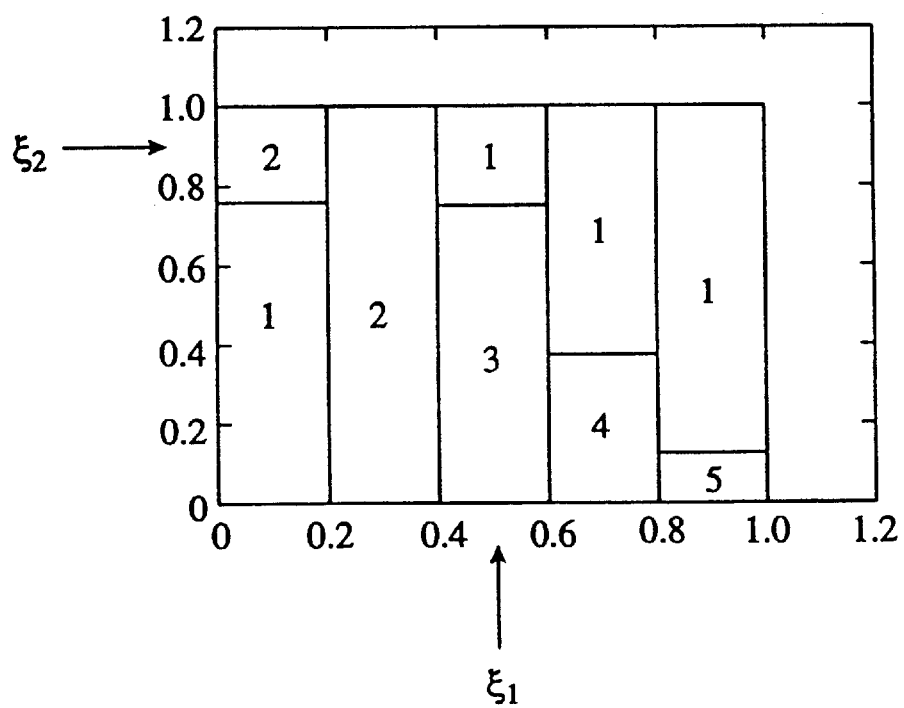

The alias-sampling method is a two-stage process. The first stage is performed as a preprocessing step, and is the remapping of the original distribution, shown in FIG. 17A, into the tableau form shown in FIG. 17B. The second stage occurs during the runtime of the Monte Carlo calculation. Two random numbers ξ1 and ξ2 are generated. ξ1 is used to select one of the columns of the tableau. ξ2 is compared to the cutoff-level of this column, and depending on the result, either the lower or upper bin index is returned. Thus, for the example shown, the pair of numbers (ξ1, ξ2)=(0.5, 0.9) indicates that "Bin 1" of FIG. 17a is selected. Similarly, the pair of numbers (ξ1, ξ2)=(0.9, 0.07) indicates that "Bin 5" of FIG. 17A should be selected.

As seen in FIG. 17B, the tableau-form of the probability distribution requires three arrays: one array for the bin edges, one array to hold the cutoff-levels, and one array to hold the "upper-bin" values. The latter two arrays are obtained during the preprocessing stage of the alias method. The preprocessing stage is an iterative process, in which "height" is transferred from "high" bins to "low" ones. The steps are described below and are summarized in Table IV.

TABLE IV

| STEP | BIN CONTENTS | | | | | SELECTED BINS | | CUTOFF LEVEL | | | | | UPPER BIN INDEX | | | | |
|---|---|---|---|---|---|---|---|---|---|---|---|---|---|---|---|---|---|
| | 1 | 2 | 3 | 4 | 5 | HIGH | LOW | 1 | 2 | 3 | 4 | 5 | 1 | 2 | 3 | 4 | 5 |
| 0 | 2.55 | 1.25 | 0.7 | 0.4 | 0.1 | 1 | 3 | — | — | — | — | — | — | — | — | — | — |
| 1 | 2.25 | 1.25 | 1.0 | 0.4 | 0.1 | 1 | 4 | — | — | 0.75 | — | — | — | — | 1 | — | — |
| 2 | 1.65 | 1.25 | 1.0 | 1.0 | 0.1 | 1 | 5 | — | — | 0.75 | 0.4 | — | — | — | 1 | 1 | — |
| 3 | 0.75 | 1.25 | 1.0 | 1.0 | 1.0 | 2 | 1 | — | — | 0.75 | 0.4 | 0.1 | — | — | 1 | 1 | 1 |
| 4 | 1.0 | 1.0 | 1.0 | 1.0 | 1.0 | — | — | 0.75 | 1.0 | 0.75 | 0.4 | 0.1 | 2 A | — | 1 | 1 | 1 |

1. find the highest remaining bin, and the first bin whose height is less than the average. For the distribution shown in FIG. 17A, these are bins 1 and 3, respectively, for the first iteration.
2. add enough "height" from the "high" bin to bring the "low" bin up to the average. The anti-alias index for what was the "low" bin has now been defined.
3. reduce the "height of the "high" bin by the amount used in step 2.
4. go to Step 1, and repeat until all bins have either been "raised" or "lowered" to the average "height", as the case may be.

While the example used in this section was a histogram distribution with uniform bin widths, the alias sampling method has been extended to piecewise-linear functions with non-uniformly spaced abscissae.

The foregoing description of the invention has been presented for purposes of illustration and description and is not intended to be exhaustive or to limit the invention to the precise form disclosed. Many modifications and variations are possible in light of the above teaching. The embodiments were chosen and described to best explain the principles of the invention and its practical application to thereby enable others skilled in the art to best use the invention in various embodiments and with various modifications suited to the particular use contemplated. The scope of the invention is to be defined by the following claims.

What is claimed is:

1. A method for calculating the phase-space information of an accelerator treatment head, comprising:
    obtaining the output data files of a specific radiation accelerator head;
    converting said output data files into correlated histograms which may be efficiently sampled to generate accurate particle phase space information during a dose calculation, wherein said histograms describe at least one subsource,
    wherein the step of converting said output data files into correlated histograms comprises:
        calculating the maximum tile radius needed for each said at least one subsource;
        calculating the radial limits of each tile of each said at least one subsource;
        estimating the position of the source plane for each said tile of each said at least one subsource;
        determining the high-end cutoff value for $R_{start}$ for each said tile of each said at least one subsource; and
        fine-tuning the $z_{start}$ for each said tile of each said at least one subsource;
    calculating said correlated histograms for each said at least one subsource with said maximum tile radius, said radial limits, said source plane, said high-end cutoff value for $R_{start}$ and said $z_{start}$; and
    calculating said phase-space information for said specific radiation accelerator head from said correlated histograms for particles, from said specific radiation accelerator head, having a high probability of going through an aperture defined by a set of jaws.

2. The method of claim 1, wherein said output data files are obtained through Monte Carlo simulation of the radiation output of said specific radiation accelerator treatment head.

3. The method of claim 1, wherein the step of converting said output data files into correlated histograms requires five passes through said output data files.

4. The method of claim 1, wherein said correlated histograms comprise energy, angle and radial probability information of particles from each said at least one subsource, wherein the step of converting said output data file(s) into correlated histograms includes the step of binning said energy, angle and radial probability information of said particles into histograms.

5. The method of claim 1, further comprising determining the amount of energy or number of particles from each said subsource that will arrive at the isocenter plane.

6. The method of claim 5, wherein the step of determining the amount of energy or number of particles from each said at least one subsource that will arrive at the isocenter plane comprises:
    using the jaw positions specified in a treatment plan, determining the limits of the $(x_{Iso}, y_{Iso})$ sampling areas for each said at least one subsource;
    calculating from said limits of the $(x_{Iso}, y_{Iso})$ sampling areas for each subsource the $(x_{Iso}, y_{Iso})$ sampling areas; and
    calculating, from said $(x_{Iso}, y_{Iso})$ sampling areas, relative energy or number of particles delivered to the isocenter plane from each said at least one subsource.

7. The method of claim 6, further comprising calculating, using said relative energy delivered to the isocenter plane, the absolute energy or number of particles delivered to the isocenter plane.

8. The method of claim 7, further comprising repeating the step of calculating the absolute energy or number of particles delivered to the isocenter plane for a plurality of subsources.

9. The method of claim 7, further comprising repeating the step of calculating the absolute energy or number of particles delivered to the isocenter plane for as many subsources as can be identified.

10. The method of claim 1, wherein said at least one subsource is selected from a group consisting of a target, a collimator and a flattening filter.

11. The method of claim 1, wherein the step of calculating the phase-space information for said specific radiation accelerator head from said correlated histograms comprises generating the (x,y) position of a particle trajectory's intersection with the isocenter plane with said limits of the $(x_{Iso}, y_{Iso})$ sampling areas for each said at least one subsource.

12. The method of claim 1, wherein the step of calculating the phase-space information for said specific radiation accelerator head from said correlated histograms comprises determining, from a particles (x,y) position, a distance $R_{Iso}$ and angle $\Phi_{Iso}$ on the isocenter plane.

13. The method of claim 1, wherein the step of calculating the phase-space information for said specific radiation accelerator head from said correlated histograms comprises adjusting a particle's Monte Carlo weight to account for the non-uniform energy fluence or number fluence of a subsource on the isocenter plane, based on $R_{Iso}$.

14. The method of claim 1, wherein the step of calculating the phase-space information for said specific radiation accelerator head from said correlated histograms comprises using $R_{Iso}$ to select a set of correlated histograms describing energy, angle, and radial probability information appropriate to a particle from a particular subsource, incident on the isocenter plane at this specific $R_{Iso}$.

15. The method of claim 1, wherein said correlated histograms are sampled to obtain energy, $R_{start}$, and $\phi_{rel}$ of a particle.

16. The method of claim 1, wherein the step of calculating the phase-space information for said specific radiation accelerator head from said correlated histograms comprises using $R_{start}$, $\phi_{rel}$ and $\Phi_{Iso}$ to calculate $X_{start}$ and $Y_{start}$ for a particle, at $Z_{start}$ location.

17. The method of claim 1, wherein a PEREGRINE-specified plane is a plane where PEREGRINE starts to track a particle through air towards a patient, wherein the step of calculating the phase-space information for said specific radiation accelerator head from said correlated histograms comprises using the values of $X_{start}$, $Y_{start}$, $Z_{start}$, $x_{Iso}$, $y_{Iso}$ and the known $z_{Iso}$ for a specific accelerator to determine a particle trajectory's intersection with said PEREGRINE-specified plane.

18. The method of claim 1, wherein the step of calculating the phase-space information for said specific radiation accelerator head from said correlated histograms comprises using the values of $X_{start}$, $Y_{start}$, $Z_{start}$, $x_{Iso}$, $y_{Iso}$ and the known $z_{Iso}$ value for a specific accelerator head to determine a particle trajectory's direction cosines at said particle's trajectory position on a PEREGRINE-specified plane.

19. The method of claim 1, wherein the step of calculating the phase-space information comprises the steps of:
    determining for a given set of jaw positions specified by a treatment plan an amount of energy or number of particles from each said at least one subsource that will arrive at the isocenter plane;

using said amounts of energy or number of particles to determine a relative probability for sampling each said at least one subsource describing said radiation accelerator head;

sampling from each said at least one subsource, using said relative probability;

using jaw positions specified in said treatment plan to determine limits of the ($x_{Iso}$, $y_{Iso}$) sampling areas for each said at least one subsource;

calculating from said limits of the ($x_{Iso}$, $y_{Iso}$) sampling areas for each said at least one subsource an ($x_{Iso}$, $y_{Iso}$) position on said isocenter plane;

calculating from said ($x_{Iso}$, $y_{Iso}$) position on said isocenter plane a distance $R_{Iso}$ and $\Phi_{Iso}$ on said isocenter plane;

adjusting a particle's Monte Carlo weight to account for the non-uniform energy fluence or number fluence of each said at least one subsource on said isocenter plane, based on $R_{Iso}$;

using a specific $R_{Iso}$ to select a set of correlated histograms describing energy, angle, and radial probability information appropriate to a particle from a particular subsource of said at least one subsource, incident on said isocenter plane at specific $R_{Iso}$;

sampling said set of correlated histograms to obtain energy, $R_{start}$, and $\phi_{rel}$ of a particle;

using $R_{start}$, $\phi_{rel}$ and $\Phi_{Iso}$ to calculate an $X_{start}$ and a $Y_{start}$ for said particle, at the $Z_{start}$ location;

using the values of said $X_{start}$, $Y_{start}$, $Z_{start}$, $x_{Iso}$, $y_{Iso}$ and the known $z_{Iso}$ for a specific accelerator to determine a particle trajectory's intersection with a PEREGRINE-specified plane; and using the values of $X_{start}$, $Y_{start}$, $Z_{start}$, $x_{Iso}$, $y_{Iso}$ and the known $z_{Iso}$ value for a specific accelerator to determine a particle trajectory's direction cosines at said particle's trajectory position on said PEREGRINE-specified plane.

* * * * *